(12) United States Patent
Tanaka et al.

(10) Patent No.: US 7,101,357 B2
(45) Date of Patent: Sep. 5, 2006

(54) DISPOSABLE EXCRETA MANAGEMENT DEVICE

(75) Inventors: Masato Tanaka, Akashi Hyogo (JP); Douglass Scott Henry, West Chester, OH (US); Yuko Tanaka, Kobe Hyogo (JP)

(73) Assignee: Procter and Gamble, Cincinnati, OH (US)

(*) Notice: Subject to any disclaimer, the term of this patent is extended or adjusted under 35 U.S.C. 154(b) by 0 days.

(21) Appl. No.: 10/367,391

(22) Filed: Feb. 14, 2003

(65) Prior Publication Data

US 2003/0150050 A1 Aug. 14, 2003

Related U.S. Application Data

(60) Provisional application No. 60/356,901, filed on Feb. 14, 2002.

(51) Int. Cl.
*A61F 5/44* (2006.01)

(52) U.S. Cl. ............................ 604/338; 604/355

(58) Field of Classification Search ........... 604/277, 604/332–344, 355, 385.19, 345–353; 600/29; 4/144.1, 144.2, 144.3, 144.4
See application file for complete search history.

(56) References Cited

U.S. PATENT DOCUMENTS

| | | | |
|---|---|---|---|
| 2,741,247 A | | 4/1956 | Marsan |
| 3,577,989 A | | 5/1971 | Anderson |
| 3,734,096 A | * | 5/1973 | Millenbach .............. 604/355 |
| 3,772,712 A | * | 11/1973 | Renn et al. .............. 4/484 |
| 3,908,658 A | * | 9/1975 | Marsan ................... 604/336 |
| 4,095,599 A | | 6/1978 | Simonet-Haibe |
| 4,344,434 A | * | 8/1982 | Robertson ............... 604/334 |
| 4,553,969 A | * | 11/1985 | Taylor .................... 604/355 |
| 4,720,880 A | * | 1/1988 | Barreau .................. 4/661 |
| 4,826,495 A | * | 5/1989 | Petersen ................. 604/333 |
| 4,874,380 A | * | 10/1989 | Hesketh .................. 604/180 |
| 5,013,307 A | * | 5/1991 | Broida .................... 604/338 |
| 5,203,806 A | * | 4/1993 | Broida .................... 604/338 |
| 5,364,379 A | * | 11/1994 | Ozenne et al. .......... 604/342 |
| 5,545,154 A | * | 8/1996 | Oberholtzer ............ 604/336 |
| 5,629,079 A | * | 5/1997 | Battles et al. ........... 442/60 |

(Continued)

FOREIGN PATENT DOCUMENTS

CN  1233945 A  11/1999

(Continued)

OTHER PUBLICATIONS

Search report for Int'l Appl. WO 03/068116 A1, Tanaka et al., Aug. 2003.*

*Primary Examiner*—Tatyana Zalukaeva
*Assistant Examiner*—Michael G. Bogart
(74) *Attorney, Agent, or Firm*—George H. Leal; Thibault Fayette; Matthew P. Fitzpatrick

(57) ABSTRACT

The disposable excreta management device has a longitudinal centerline, a transverse centerline, a wearer facing surface and an opposing surface. The disposable excreta management device comprises a flexible bag to contain excreta and an adhesive flange to attach the device to the body of a wearer. The flexible bag has an opening surrounded by the adhesive flange. The adhesive flange has an outer periphery and an inner periphery. The adhesive flange comprises an adhesive layer and a substrate. The substrate has at least one base-slit extending from the outer periphery to the inner periphery along the longitudinal centerline. Alternatively, the adhesive layer may have a surface-slit extending from the outer periphery to the inner periphery along the longitudinal centerline and the surface-slit is positioned between an anus and a urethra when the device is worn.

7 Claims, 20 Drawing Sheets

U.S. PATENT DOCUMENTS

| | | | |
|---|---|---|---|
| 5,718,696 A * | 2/1998 | Kollerup | 604/339 |
| 6,015,399 A * | 1/2000 | Mracna et al. | 604/332 |
| 6,129,716 A * | 10/2000 | Steer | 604/333 |
| 6,485,467 B1 * | 11/2002 | Crook et al. | 604/174 |
| 6,485,476 B1 * | 11/2002 | von Dyck et al. | 604/332 |
| 6,551,292 B1 * | 4/2003 | D'Acchioli et al. | 604/329 |
| 6,685,687 B1 * | 2/2004 | Mishima et al. | 604/385.19 |
| 6,764,474 B1 * | 7/2004 | Nielsen et al. | 604/344 |
| 2003/0045843 A1 * | 3/2003 | Kondo et al. | 604/332 |
| 2003/0208170 A1 * | 11/2003 | D'Acchioli et al. | 604/355 |

FOREIGN PATENT DOCUMENTS

| | | | |
|---|---|---|---|
| GB | 2 152 387 A | | 8/1985 |
| JP | 2002-191631 | * | 7/2002 |
| JP | 2002-272766 | * | 9/2002 |
| WO | WO 98/17212 | | 4/1998 |

* cited by examiner (a)

(b)

(a)

(b)

(c)

(a)

(b)

(a)

(b)

(a)

(b)

DISPOSABLE EXCRETA MANAGEMENT DEVICE

CROSS REFERENCE TO RELATED APPLICATION

This application claims the benefit of U.S. Provisional Application No. 60/356,901, filed on Feb. 14, 2002.

FIELD OF THE INVENTION

The present invention relates to an excreta management device used for babies, children or adults. More particularly, the present invention relates to an excreta management device comprising a flexible bag and an adhesive flange capable of conforming movement of a wearer and preventing detachment of the adhesive flange during use of the device.

BACKGROUND

Excreta management devices are known as articles that are designed to be worn principally by incontinence sufferers and in particular by bedridden patients. Such excreta management devices are attached to the perianal area or urethral area of a wearer and are intended to entrap and immediately contain fecal material, urine and other bodily discharges.

A representative excreta management device is disclosed in, e.g. U.S. Pat. No. 3,577,989. It discloses a disposable elimination-trapping bag comprising a sack having an open-top portion and a thin annular oval-shaped flange secured to the sack around the open-top portion. The flange comprises a layer of adhesive material as a means of attaching the disposable bag to a wearer. The disposable bag is specifically designed for attachment to a wearer in the vicinity of the anus.

Another representative excreta management device is disclosed in, e.g. UK Patent Application No. GB 2152387A. It discloses a fecal collector comprising an elongate bag and a flat ring. The elongate bag comprises a pair of panels of thermoplastic sheet joined at their margins such that the bag has an opening at one end thereof. The surface of the flat ring is coated with a layer of pressure-sensitive and water-resistant adhesive. The inner margin of the flat ring defines a generally circular aperture that is directly aligned with the opening of the elongate bag. The flat ring and the elongate bag are secured together along the inner margin of the ring. The flat ring of the fecal collector is adhesively attached to the perianal area of a wearer.

A problem naturally associated with such a device is its attachment to the human body. The approach mostly used in the field is to provide the device with an adhesive flange sticking to the perianal or urethral area. The complete attachment of the device to the desired area of the skin of a wearer is a key point in the excreta management device comprising an adhesive flange. Incomplete attachment of the device leads to a serious problem, in particular, incomplete collection of feces/urine and leakage of feces/urine. For example, if the adhesive flange of an excreta management device is not completely attached to the skin around an excretory orifice (e.g., an anal orifice or a urethra orifice) of a wearer, excreta such as feces or urine intrude between the flange and the skin, and then substantial pressure occurs toward the flange of the device during the defecation process. Such substantial pressure results in the detachment of the adhesively secured device.

As disclosed in the above prior arts, an adhesive flange used for an excreta management device conventionally has an opening positioned at the center of the flange, and comprises a substrate continuously surrounding the opening and an adhesive layer supported by the substrate. The substrate to support the adhesive layer conventionally is made from inelastic materials such as nonwoven materials, foams or plastic films. The adhesive layer is applied on the substrate such that the adhesive layer continuously surrounds the opening. Therefore, the adhesive flange is adhesively attached to the skin in whole circumference of an excretory orifice when the device is worn.

In such a conventional adhesive flange, it has been recognized that the adhesive flange often/sometimes detaches from the wearer's skin during use of the device due to skin movement caused by a wearer's motion such as walking, crawling, running, sitting and defecating. This is because the adhesive flange does not sufficiently conform to such movement of the skin of a wearer due to inelasticity of the substrate of the adhesive flange continuously attached to the skin in whole circumference of an excretory orifice. If intense skin movements happen during use of the device, the conventional substrate tends to prevent the adhesive flange from following such skin movements. This results in partial/complete detachment (i.e., the above-mentioned "incomplete attachment") of the adhesive flange from the wearer's skin. Such detachment leads to incomplete-collection/leakage of excreta, and often/sometimes makes the wearer feel even skin pain when the detachment of the adhesive flange happens. Particularly, detachment of the adhesive flange at a perineum (i.e., region between an anus and a urethral orifice) tends to provide the wearer with serious skin pain since a perineum is usually very sensitive.

In case of female wearers having genitalia at a perineum, attachment of the adhesive flange at a perineum provides serious discomfort. In addition, discharged urine tends to flow to a perineum since a female wearer has a urethral orifice close to a perineum. This could result in contact of the adhesive layer constituting the adhesive flange with urine. The contact of the adhesive layer with urine facilitates detachment of the adhesive flange at a perineum and leads to deterioration of the adhesive layer.

Accordingly, there still exists a need for an excreta management device which conforms movement of a wearer such that the device continues to be surely attached to the desired area of the skin of a wearer during use of the device, and which does not provide a wearer with discomfort and skin pain during use of the device.

SUMMARY

The disposable excreta management device has a longitudinal centerline, a transverse centerline, a wearer facing surface and an opposing surface. The disposable excreta management device comprises a flexible bag to contain excreta and an adhesive flange to attach the device to the body of a wearer. The flexible bag has an opening surrounded by the adhesive flange. The adhesive flange has an outer periphery and an inner periphery. The adhesive flange comprises an adhesive layer and a substrate. The substrate has at least one base-slit extending from the outer periphery to the inner periphery along the longitudinal centerline. Alternatively, the adhesive layer may have a surface-slit extending from the outer periphery to the inner periphery along the longitudinal centerline and the surface-slit is positioned between an anus and a urethra when the device is worn.

BRIEF DESCRIPTION OF THE DRAWINGS

While the Specification concludes with claims which particularly point out and distinctly claim the invention, it is believed the present invention will be better understood from the following description of preferred embodiments taken in conjunction with the accompanying drawings, in which like reference numerals identify identical elements and wherein:

DETAILED DESCRIPTION

All cited references are incorporated herein by reference in their entireties. Citation of any reference is not an admission regarding any determination as to its availability as prior art to the claimed invention.

The definitions of several terms are first provided to assist the reader in understanding the present invention.

The term "comprising" means that other steps and other ingredients which do not affect the end result can be added. This term encompasses the term "consisting of" and "consisting essentially of".

The term "disposable" as used herein, describes devices which generally are not intended to be laundered or otherwise restored or reused (i.e., they are intended to be discarded after a single use and, preferably, to be recycled, composted or otherwise disposed of in an environmentally compatible manner.)

The term "excreta" or "bodily discharges", as used herein, are interchangeable, and includes all discharges released from an excretory orifice of a human body, including fecal materials, urine, menses, and the like. The term "excretory orifice", as used herein, refers to an orifice which excreta pass through to discharge the excreta from the human body when excretion occurs. Such an excretory orifice includes urethra, vaginal orifice, anus, and the like.

Figure 1:
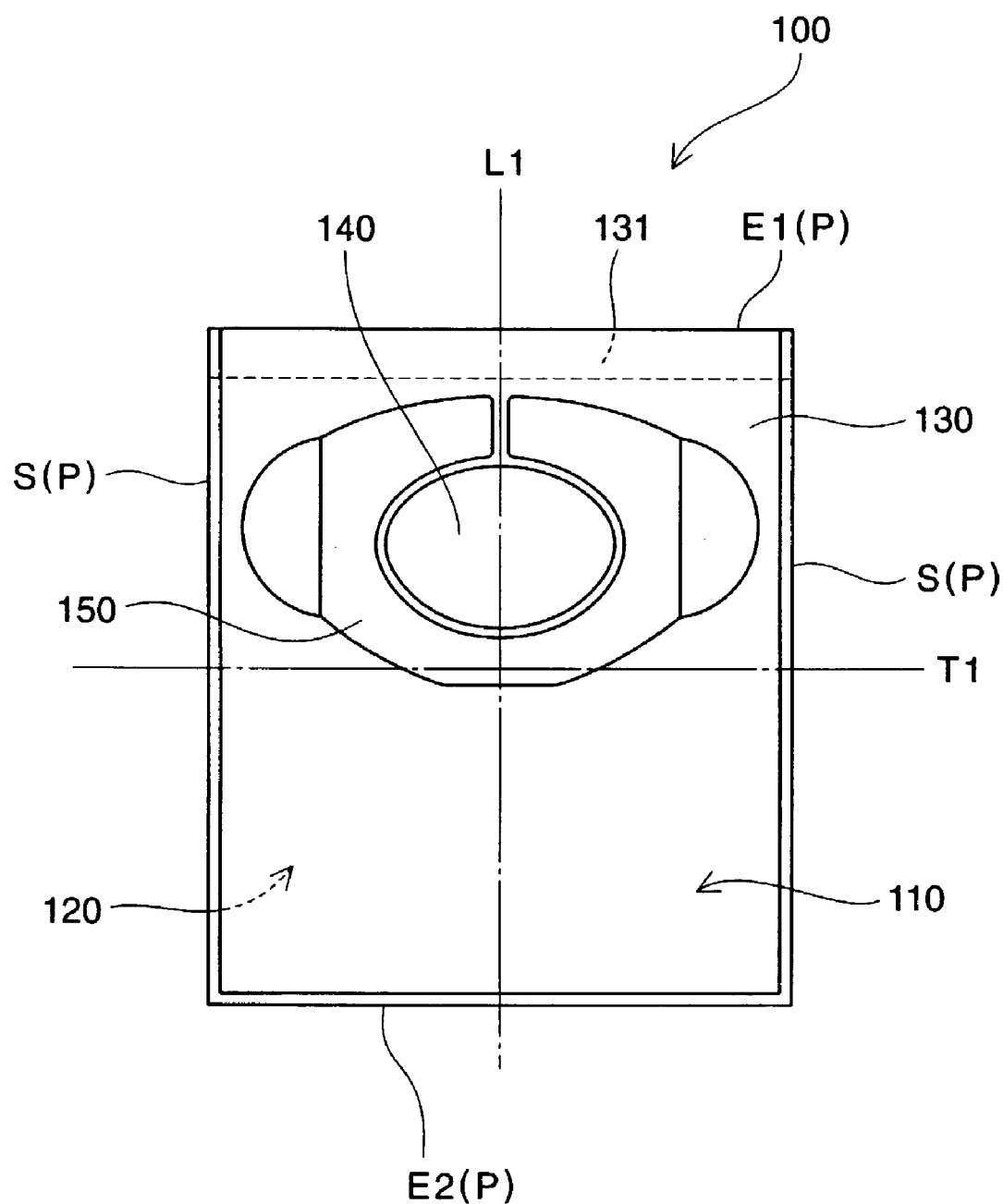
FIG. 1 is a top plan view of one embodiment of an excreta management device of the present invention.
Figure 2:
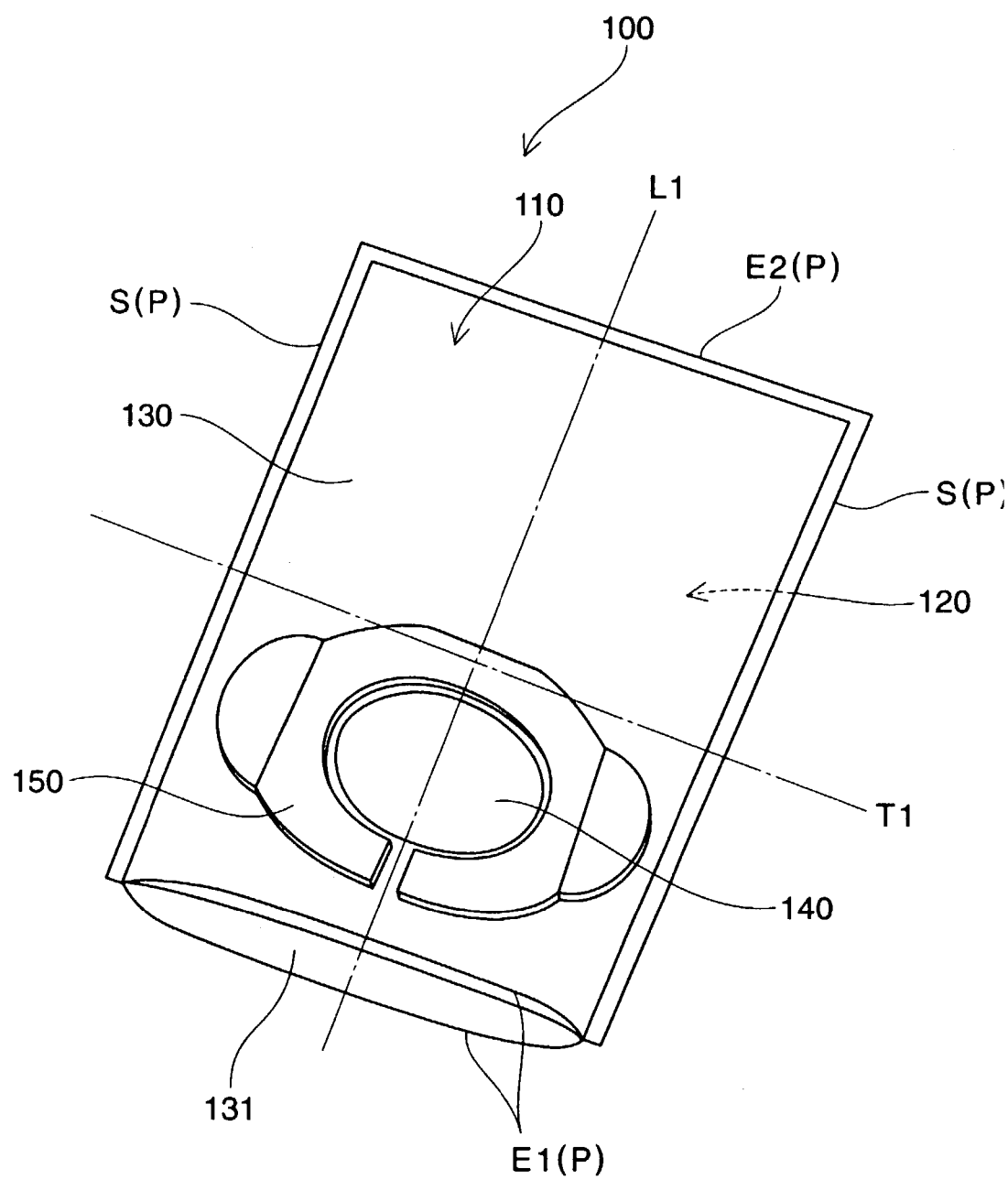
FIG. 2 is a perspective view showing the wearer-facing surface of the excreta management device of FIG. 1.
Figure 3:
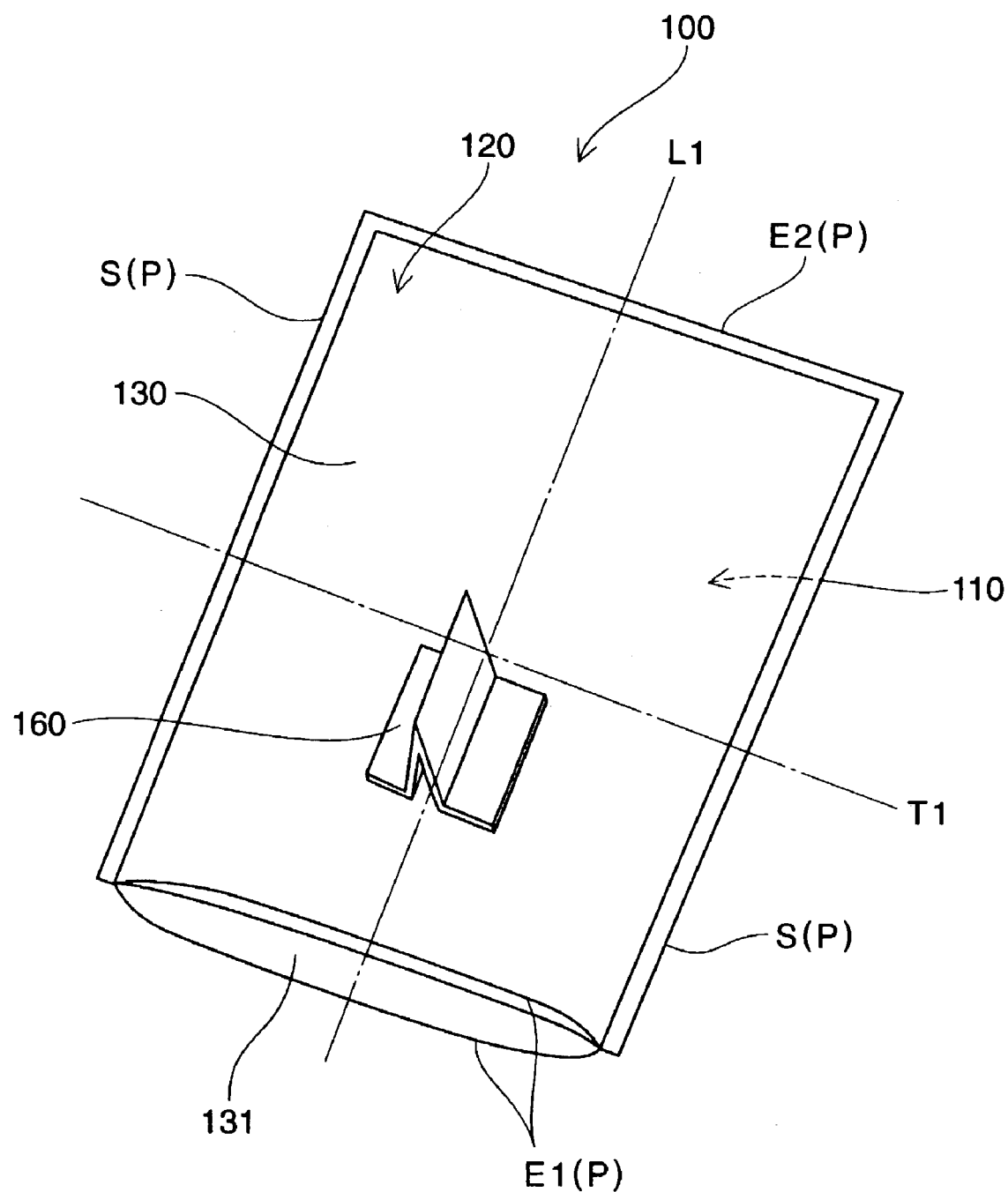
FIG. 3 is a perspective view showing the opposing surface of the excreta management device of FIG. 1.

FIGS. 1 to 3 show one embodiment of a disposable excreta management device of the present invention which is disposed to the skin around the excretory orifice (e.g., a perianal area) of a wearer. The excreta management device 100 shown in FIGS. 1 to 3 has a longitudinal centerline L1. The term "longitudinal", as used herein, refers to a line, axis or direction in the plane of the device 100 that is generally aligned with (e.g., approximately parallel to) a vertical plane which bisects a standing wearer into left and right body halves when the disposable excreta management device 100 is worn. The excreta management device 100 shown in FIGS. 1 to 3 also has a transverse centerline T1. The terms "transverse" or "lateral", as used herein, are interchangeable, and refer to a line, axis or direction which lies within the plane of the disposable excreta management device 100 that is generally perpendicular to the longitudinal direction. The excreta management device 100 shown in FIGS. 1 to 3 has two surfaces; one is a wearer-facing surface 110 and the other is an opposing surface 120. The wearer-facing surface 110 is the surface of the device 100 which is generally oriented toward the wearer when the device 100 is worn. The wearer-facing surface 110 typically at least partially comes in contact with the wearer's skin during use of the device 100. The opposing surface 120 is the surface of the device 100 which is generally oriented away from the wearer when the device 100 is worn, and at least partially toward a garment if a garment is worn. The excreta management device 100 comprises a flexible bag 130 having an opening 140, an adhesive flange 150 surrounding the opening 140 and an assistant tab 160 disposed on the opposing surface 120 of the device 100.

The flexible bag 130, as used herein, is a flexible receptacle for the containment of discharged excreta, such as fecal materials, urine or the like. The bag 130 can be provided in any shape or size depending on the intended use thereof, i.e., whether the device is intended for bedridden patients or active patients suffering from incontinence. For example, elongated bags which are principally tubular or rectangular are typically utilized by bedridden patients and elderly incontinence sufferers. For more active wearers such as infants or adults, the excreta management device 100 should preferably be anatomically shaped such that the device 100 follows the contours of the body and can be worn inconspicuously by the wearer under normal garments. Particularly, preferred shapes are three-dimensional shaped bags such as cubic shaped bags, spherical shaped bags, conical (or truncated conical) shaped bags, pyramidal (or truncated pyramidal) shaped bags, tetrahedral (or truncated tetrahedral) shaped bags, cylindrical shaped bags or the like. Further, when the bag is not expanded, the bag may have a substantial circular, oval, square, rectangular, polygonal shape.

In a preferred embodiment shown in FIGS. 1 to 3, the bag 130 is a rectangular shape which is longitudinally/transversely symmetric when the bag 130 is not expanded. The bag 130 has side edges S extending in the longitudinal direction, end edges E1 and E2 extending in the transverse direction and a folded gusset panel 131 positioned at the end edge E1 as shown in FIGS. 1 to 3. The side edges S and the end edges E1 and E2 correspond to longitudinal end and transverse end of the bag 130 respectively to define the periphery P of the bag 130.

The bag 130 is preferably designed to provide sufficient volume for excreta under a variety of wearing conditions, e.g., when the device 100 is worn by active wearers (i.e., not bedridden wearers). The bag 130 is designed to safely contain any entrapped material, typically it will be liquid impermeable, yet it may be breathable. The bag 130 is designed to having sufficient strength in order to resist rupturing in use, e.g., when pressure on the bag 130 is exerted in typical wearing condition such as sitting.

Figure 4:
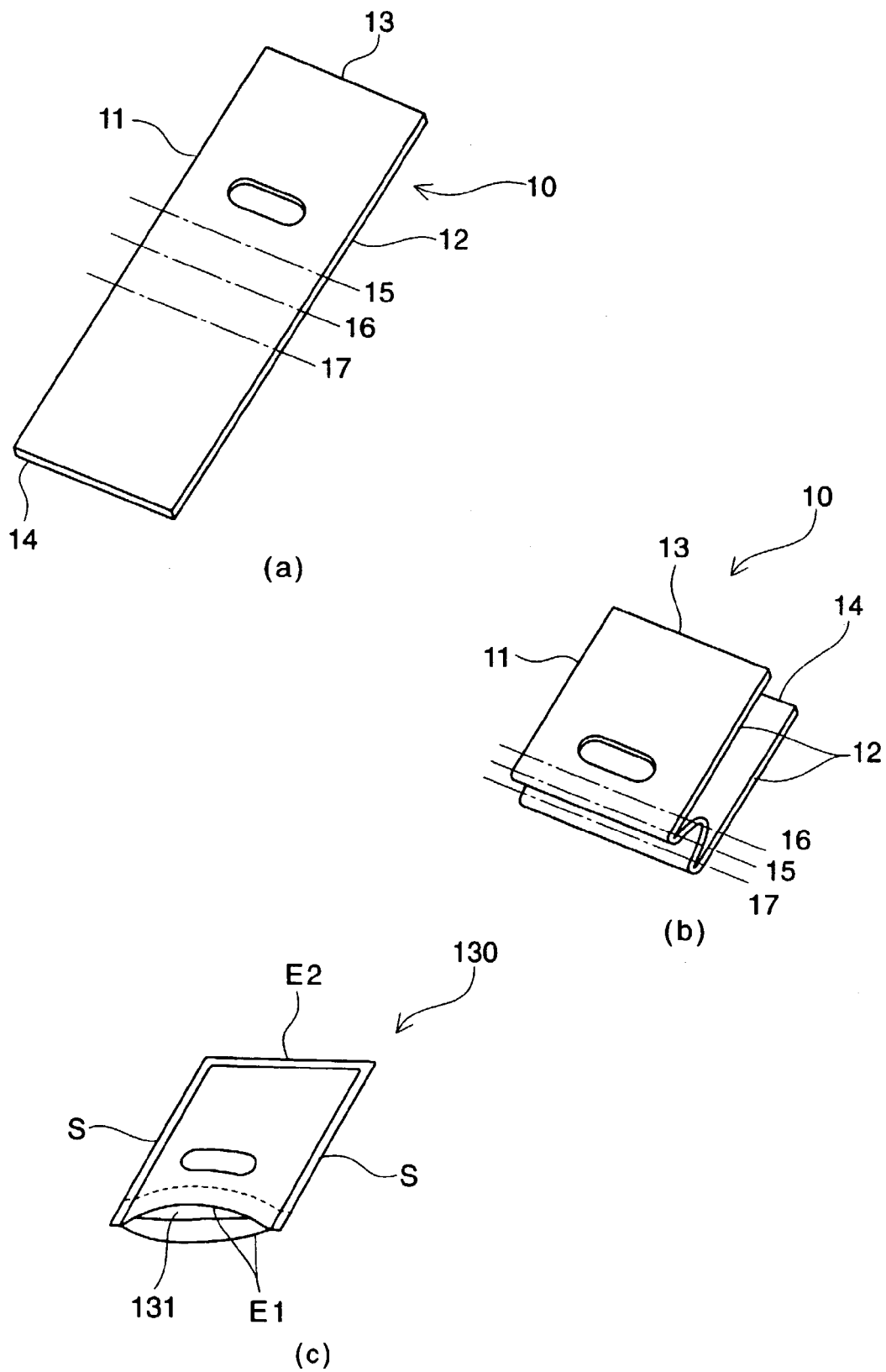
FIG. 4(a) is a first schematic view of a process for forming a flexible bag constituting the excreta management device of FIG. 1.
FIG. 4(b) is a second schematic view of a process for forming a flexible bag constituting the excreta management device of FIG. 1.
FIG. 4(c) is a third schematic view of a process for forming a flexible bag constituting the excreta management device of FIG. 1.

The bag 130 may be made from a unitary piece of material or from a number of separate pieces of material, which may be identical or different and which are sealed at their respective peripheries, depending on the shape of the bag 130 required. In a preferred embodiment shown in FIGS. 4(a) to 4(c), the bag 130 constituting the excreta management device 100 is made from a single web sheet 10. As shown in FIG. 4 (a), the web sheet 10 has longitudinal edges 11 and 12 and transverse edges 13 and 14. The web sheet 10 is folded into a "W"-like configuration along the folding lines 15, 16 and 17 as shown in FIG. 4(b). The web sheet 10 is then sealed along the longitudinal edges 11, 12 and the transverse edges 13 and 14 by means known to the person skilled in the art, such as heat seal, adhesive, or the like, in order to form the bag 130. The bag 130 produced by such a process shown in FIGS. 4(a) to 4(c) has the folded gusset panel 131 at the end edge E1. The folded gusset panel 131 allows the bag 130 to expand when the bag 130 contains discharged excreta. Such expansion of the bag 130 created by the folded gusset panel 131 provides extra storage capacity in use, and prevents undesirable detachment of the device 100 from the wearer's body even when intense gush of excreta (i.e., defecation) suddenly occurs.

Such a flexible bag, alternatively, may be made from two separate sheets. In another embodiment shown in FIGS. 5 and 6, the excreta management device 200 has a wearer-facing surface 210 and an opposing facing surface 220, and comprises a bag 230 having an opening 240, an adhesive flange 250 surrounding the opening 240 and an assistant tab 260 disposed on the opposing surface 220 of the device 200. The bag 230 is a rounded-pentagonal shape. The bag 230 is made from a wearer-facing sheet 231 and an opposing sheet 232. The wearer-facing sheet 231 and the opposing sheet 232 are sealed along the periphery P of the sheets 231 and 232 by means known to the person skilled in the art, such as heat seal, adhesive, or the like, in order to form the bag 230.

Figure 6:
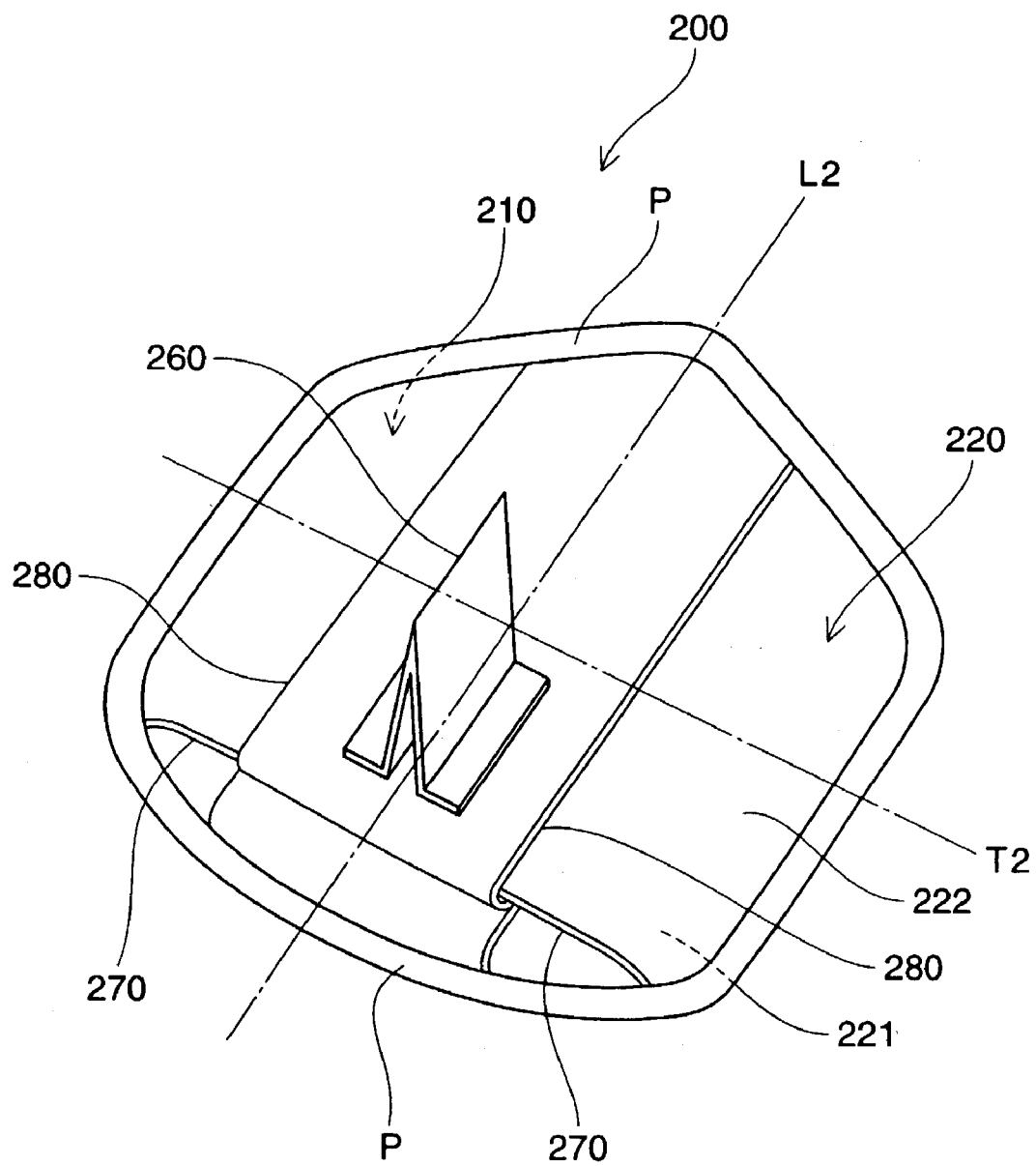
FIG. 6 is a perspective view showing the opposing surface of the excreta management device of FIG. 5.

The bag 230 preferably has at least one fold on the opposing surface 220 in order to allow the bag 230 to expand vertically when the bag 230 contains excreta. The number of the fold will obviously depend upon the circumstances, e.g., a configuration of the bag, a size of the bag and/or a material of the bag. In the embodiment shown in FIG. 6, folds 270 and 280 are formed on the opposing surface 220 of the device 200 such that the bag 230 can expand vertically to have a three-dimensional shape when defecation occurs. The expansion of the bag 230 provides extra storage capacity in use. The fold 270 has an alphabet "Z"-like configuration in the cross-sectional view of the opposing surface 220 of the device 200 taken along the longitudinal centerline L2. Thus, such a fold is referred to as "Z-fold" herein. In the embodiment as shown in FIG. 6, one Z-fold oriented in the transverse direction is formed on the opposing surface 220 of the device 200. The other folds 280, 280 oriented in the longitudinal direction are formed on the opposing surface 220 of the device 200 as shown in FIG. 6. The folds 280, 280 comprise two Z-folds oriented in the longitudinal direction. The two Z-folds 280, 280 are disposed oppositely with respect to the longitudinal centerline L2 and parallel to the longitudinal centerline L2. The combination of the two opposite Z-folds has a Greek letter "Ω (OMEGA)" like configuration in the cross-sectional view of the opposing surface 220 of the device 200 taken along the transverse centerline T2. Such a combination of two opposite Z-folds is referred to as "OMEGA-fold" herein. Thus, one Z-fold 270 and one OMEGA-fold 280 are formed on the opposing surface 220 of the device 200 in the embodiment shown in FIG. 6.

The bag 130 can comprise one or multiple layers, preferably two or three layers. The layer on the inside of the bag, which will typically at least partially come in contact with excreta, is called the inner layer. The outermost layer of the bag 130, which will typically at least partially come in contact with the skin of a wearer and the garments of the wearer, is called the outer layer. The layer of the bag may be provided from any material such that the bag is liquid impervious. The layer may in particular comprise any material such as a nonwoven or a polymeric film. In a preferred embodiment, the layer may be formed from a laminate comprising a nonwoven layer and a polymeric film. The outer layer of the bag 130 is preferably provided with a nonwoven layer. The nonwoven outer layer presents a compliant surface to the skin of a wearer and thus greatly improves skin healthiness. In one preferred embodiment, the bag 130 comprises two layers, which comprises a nonwoven layer as the outer layer and a film as the inner layer. Alternatively, the bag 130 may comprise three layers; one film layer and two nonwoven layers. Preferably, the film may be interposed between the two nonwoven layers. This sequence of layers results in a closed fibrous structure, which has a particularly pleasing sensation on contact with the skin of a wearer.

Suitable nonwoven layers for the bag 130 may comprise felt fabrics, spunlaced fabrics, fluid jet entangled fabrics, air-laid fabrics, wet-laid fabrics, dry-laid fabrics, meltblown fabrics, staple fiber carding fabrics, spunbonded fabrics, stitch-bonded fabrics, apertured fabrics, combinations of the above or the like. The nonwoven layer or the nonwoven layers constituting the bag 130 may be hydrophobic or hydrophilic. For example, if the bag 130 comprises a film layer, the nonwoven layers may be hydrophilic or hydrophobic. If the bag 130 does not comprise a film layer, preferably at least one nonwoven layer is hydrophobic. It may still be desirable to make both nonwoven layers hydrophobic to ensure that the bag is liquid impervious. Typically, the nonwoven layer is treated with a surface active material, such as a fluorchemical or other hydrophobic finishings, to provide the requisite hydrophobicity. The nonwoven layer, however, may equally be treated with coatings of liquid impervious materials such as hot-melt adhesives or coatings of silicone or other hydrophobic compounds such as rubbers and vegetable and mineral waxes or it may be physically treated using nano-particulates or plasma coating techniques, for example. The nonwoven layer can also be treated with agents to improve the tactile perceivable softness. The agents include but are not limited to vegetable, animal or synthetic oils, silicone oils and the like. The presence of these agents is known to impart a silky or flannel-like feel to the nonwoven layer without rendering it greasy or oily to the tactile sense of the wearer. Additionally, surfactant material, including anionic, nonanionic, cationic and non-cationic surfactants, may be added to further enhance softness and surface smoothness. Furthermore, the nonwoven layer may be impregnated with a lotion to provide desirable therapeutic or protective coating lotion benefits. The lotion coating is transferable to the skin of a wearer by normal contact and wearer motion and/or body heat. Generally, mineral oil in the form of a lotion is recognized as being effective in imparting a soothing, protective coating to the skin of a wearer. It is also possible to impregnate the nonwoven layer with a solid oil phase of cream formulation or to incorporate into the nonwoven layer an array of pressure- or thermal- or hydrorupturable capsules containing for example, baby oil.

Suitable film materials for the bag 130 may comprise a thermoplastic material. The thermoplastic material can be selected from among all types of polyolefins especially polyethylene, polypropylene, amorphous polyolefins, and the like; material containing meltable components comprising fibers or polymeric binders including natural fibers such as cellulose—wood pulp, cotton, jute, hemp; synthetic fibers such as fiberglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., Ill., US under the designation EXXAIRE or those supplied by Mitsui Chemical Co., Japan under the designation ESPOIR NO; and monolithic breathable materials such as Hytrel™ available from DuPont and Pebax™ available from ELF Atochem, France. In a preferred embodiment, a film which is comprised in any layer is preferably permeable to gases such as air and to vapour such as water vapour in order to avoid the problem of entrapment and condensation of moisture vapour given off by the body of the wearer and thus, the hot, clammy and uncomfortable conditions after a short period of use.

The bag 130 may further contain an absorbent material may therein. The absorbent material may be positioned inside the bag 130 in any suitable manner. For example, the absorbent material may be loosely arranged within the bag 130 or may be secured to the inner side of the bag 130. Any known techniques for securing absorbent material to nonwoven and film substrates may be used to secure the absorbent material to the inner side of the bag 130. The absorbent material may also be arranged to have any desired shape or configuration (e.g., rectangular, oval, circular, etc.). The absorbent material may comprise any material which is capable of absorbing and retaining discharged body fluids. The absorbent material may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers, synthetic fibers such as crimped polyester fibers; peat moss; tissue, including tissue wraps and tissue laminates; absorbent foams; absorbent sponges; superabsorbent polymers; superabsorbent hydrogel-forming polymeric material; absorbent gelling materials; or any other known absorbent material or combinations of materials or mixtures of these. The configuration and construction of the absorbent component may also be varied (e.g., the absorbent component may have varying caliper zones (e.g., profiled so as to be thicker in the center), hydrophilic gradients, superabsorbent gradients, or may comprise one or more layers or structures.

The assistant tab 160 is disposed on the opposing surface 120 of the bag 130 as shown in FIG. 3. The assistant tab 160 is provided to expand the bag 130 into a three-dimensional shape easily by pulling the assistant tab 160 after the device 100 is attached to the wearer.

According to an alternative embodiment, the assistant tab 160 can be also provided as a handling aid for the device 100, that is as a means for holding the device 100 in order to apply it to the wearer's body, and/or to remove it after or during its use, in addition or as an alternative to its function to expand the bag 130 into a three-dimensional shape.

This alternative embodiment is described with reference to the articles illustrated in FIGS. 3 and 6, but is equally applicable to any alternative embodiments of the excreta management device according to the present invention.

As illustrated in FIGS. 3 and 6, the means 160, 260 for holding the device 100, 200 can be provided as an elongated strip of flexible material, e.g. a film material, oriented substantially perpendicularly to the longitudinal centerline L1, L2, and affixed to the opposing surface 120, 220 of the bag 130, 230 at its two ends, with the intermediate portion not joined to said opposing surface. The intermediate portion defines a space intended for insertion of at least one user's finger for holding the device 100, 200. The strip can have a length such that it projects out of the opposing surface of the bag, as shown in the FIGS. 3 and 6, or alternatively can lie flat onto that surface. Of course the means 160, 260 for holding the device 100, 200 are intended for use by the wearer him/herself, and also by a person taking care of a wearer, e.g. a nurse, who handles the device 100, 200 to apply and/or remove it to/from the wearer's body.

Figure 7:
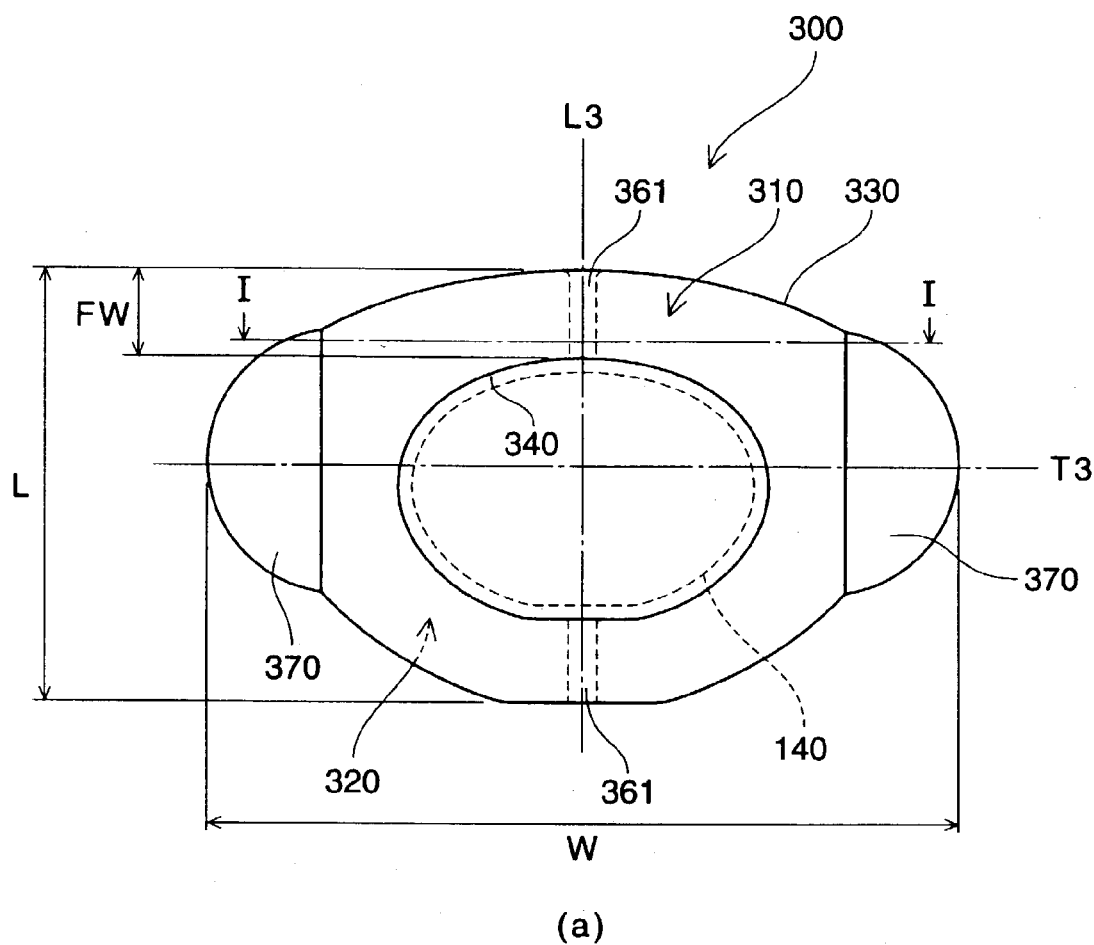
FIG. 7(a) is a top plan view of one embodiment of an adhesive flange.
FIG. 7(b) is a cross-sectional view taken along line I—I of FIG. 7(a)
Figure 7:
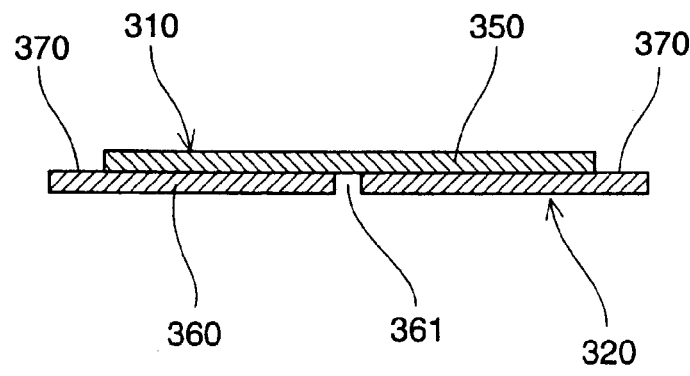
Figure 8:
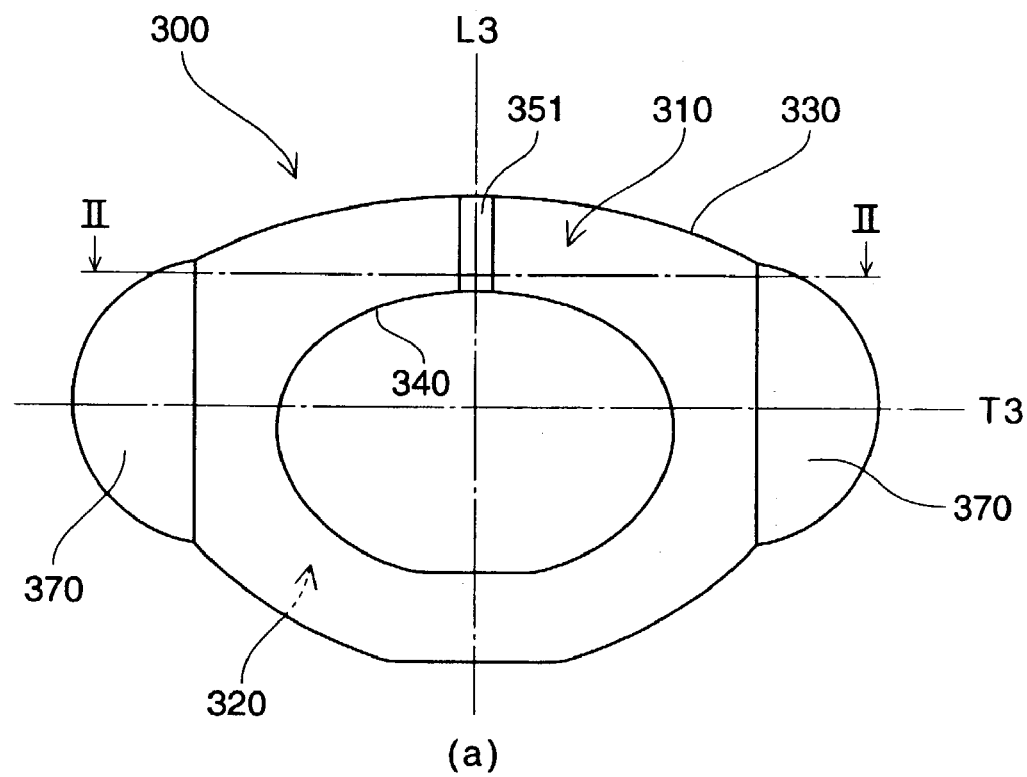
FIG. 8(a) is a top plan view of another embodiment of an adhesive flange.
FIG. 8(b) is a cross-sectional view taken along line II—II of FIG. 8(a)
FIG. 8(c) is a cross-sectional view of yet another embodiment of the adhesive flange of FIG. 8(b)
Figure 8:
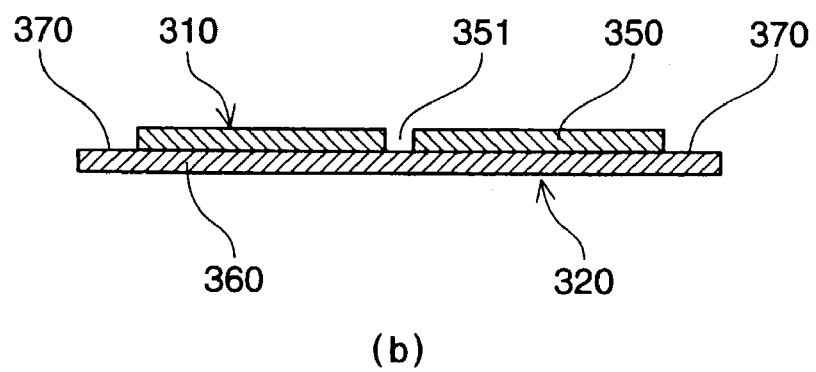
Figure 8:
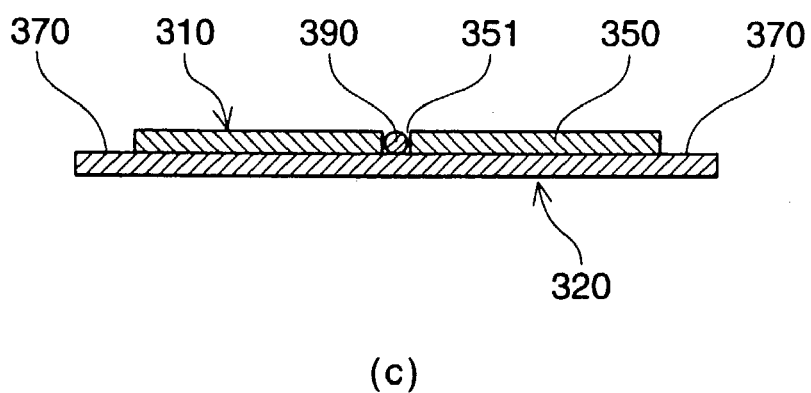
Figure 9:
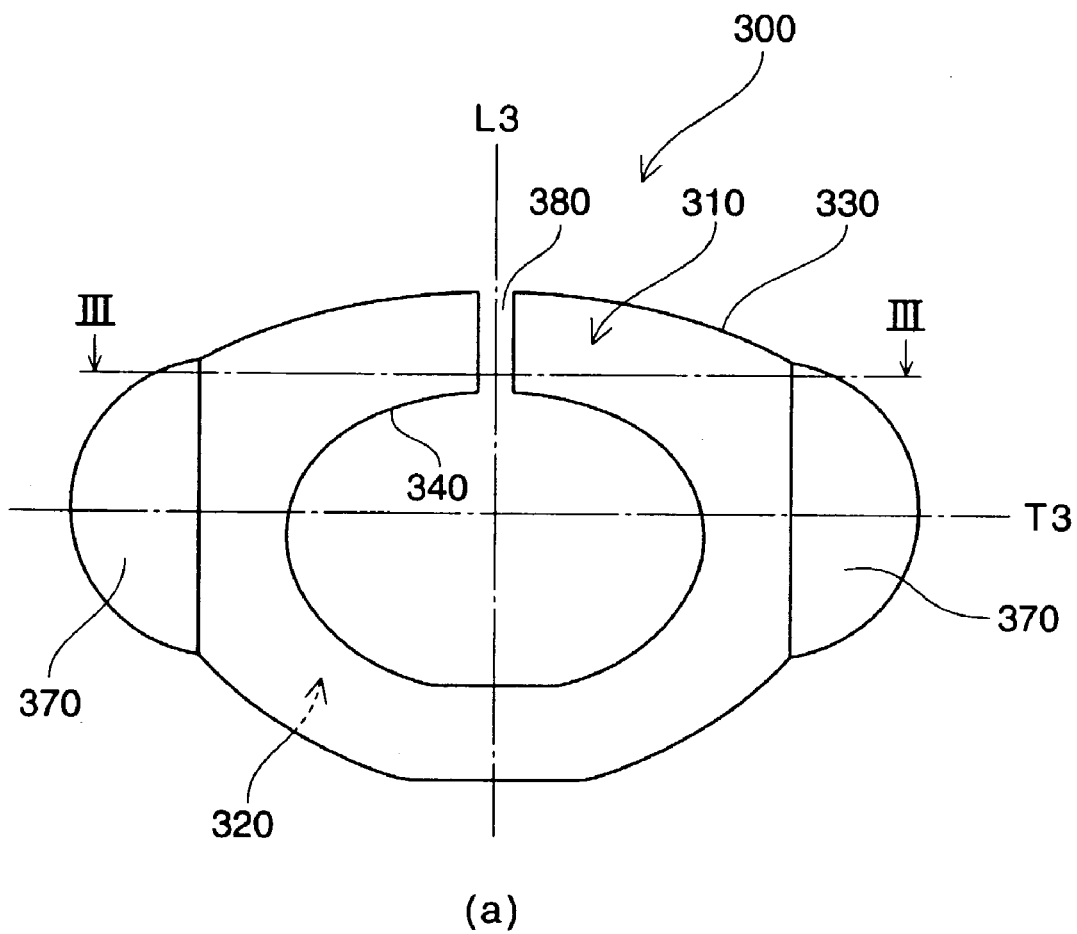
FIG. 9(a) is a top plan view of another embodiment of an adhesive flange.
FIG. 9(b) is a cross-sectional view taken along line III—III of FIG. 9(a)
Figure 9:
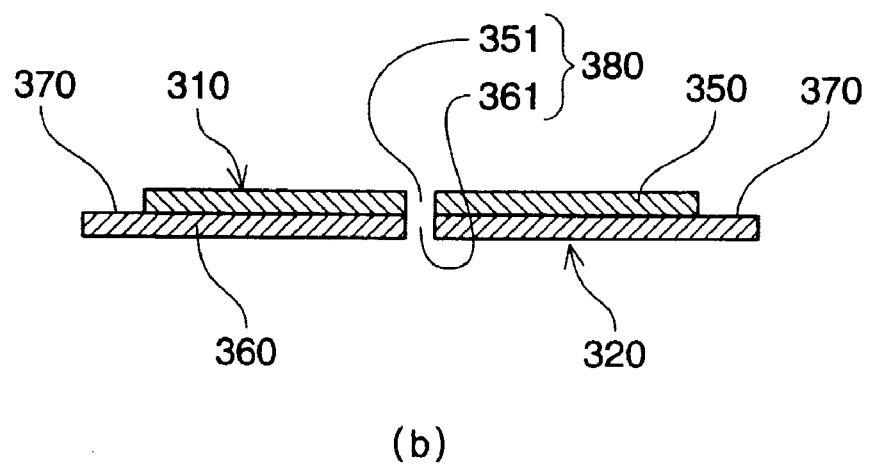
Figure 16:
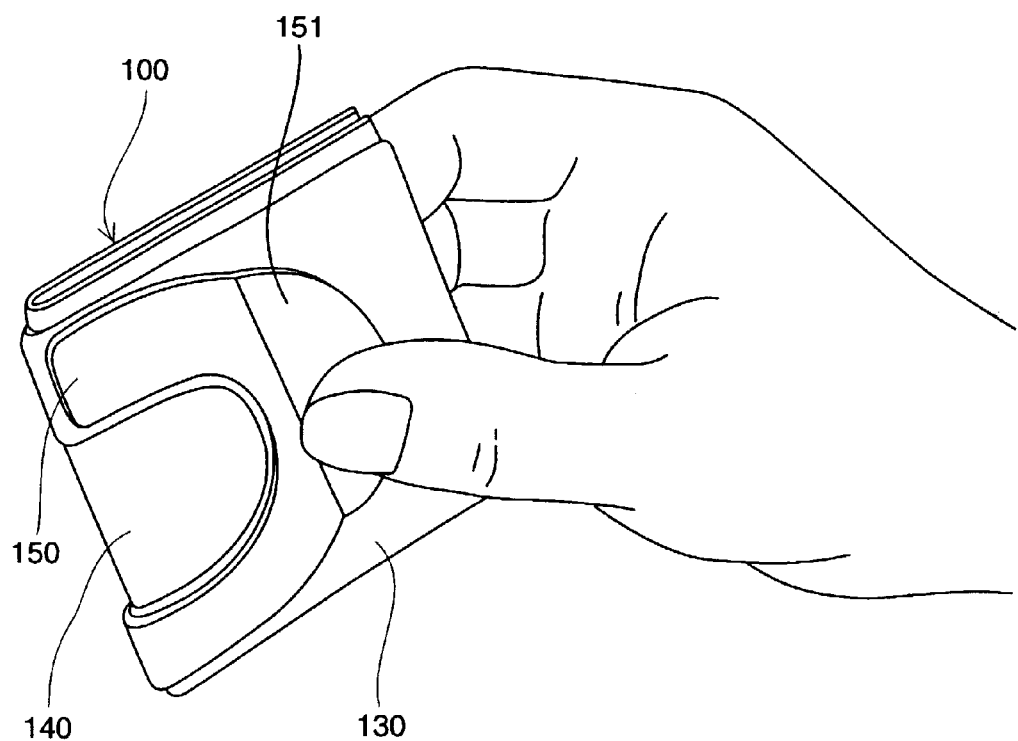
FIG. 16 is a perspective view of the excreta management device of FIG. 1 when the device is held by the user.

The assistant tab 160, 260 provided as a handling aid for application and/or removal of the device 100, 200 can of course constitute an alternative to other corresponding features described in the present application, for example with reference to the embodiment of FIG. 16 for the application of the device to the wearer's body, or with reference to the removal tabs 370 of the flange 300 as shown in FIGS. 7, 8, and 9 for the subsequent removal.

According to one possible embodiment of the present invention, the user can for example put the device 100, 200 on the palm of his/her hand with the opposing surface 120, 220 of the bag 130, 230 contacting the hand, and insert one of the fingers, e.g. the middle finger, in the space defined between the intermediate portion of the strip and the opposing surface of the device. The user can therefore hold the device 100, 200 without exerting any force, in order for example to apply the device to the wearer's body. The means 160, 260 for holding the device 100, 200 can also allow an easy removal of the device from the wearer's body, by simply inserting a finger in said space between the strip and the opposing surface 120, 220 of the bag 130, 230, and pulling said means.

In the embodiments illustrated in FIGS. 3 and 6, the means 160, 260 are typically positioned, with respect to the longitudinal direction, substantially close to the intersection of the longitudinal and transverse axes L1, L2, and T1, T2, respectively. Alternatively, the means 160, 260 can be positioned closer to, or at one of the longitudinal end edges of the device 100, 200. For example, the means 160, 260 can be positioned at the front end edge of the device 100, 200, that is at the end edge which in use corresponds to the front part of the wearer's body. In this position, the means 160, 260 are particularly useful for removal of the device 100, 200 from the wearer's body, either in case of removal after use, for the final disposal of the device, or in case of a partial removal and its subsequent reapplication during use, e.g. for inspection of the device.

According to further alternative embodiments of the present invention, the assistant tab 160, 260, consisting of an elongated strip of flexible material as illustrated in FIGS. 3 and 6, can be replaced by equivalent means allowing finger insertion for handling and holding the device, e.g. for application to the wearer's body, and/or removal therefrom.

For example, means for holding an excreta management device according to the present invention can be alternatively constituted by a pocket having an opening for finger insertion and provided onto the opposing surface of the bag. The pocket can be typically located along the longitudinal axis of the device in a position corresponding to that of the assistant tab 160, 260 in FIGS. 3 and 6, or alternatively at different locations, for example closer to, or at the front end edge of the excreta management device, as already explained above with reference to the strip of flexible material. Typically in a pocket the opening for finger insertion faces towards the center of the device, identified by the intersection of the longitudinal and transverse axes, but different arrangements are possible depending on the position of the pocket itself on the opposing surface of the bag, and on how the excreta management device has to be handled, and/or applied/removed, as can be determined by the man skilled in the art.

The pocket can be preferably provided onto the opposing surface of the bag as a separate element, for example as a sheet of flexible material suitably secured or joined in the desired location onto the opposing surface of the bag by known means, in order to define the opening for finger insertion in the desired position and orientation. Any suitable flexible material can be used, for example the same material of the bag such as a polymeric film or a nonwoven/film laminate. Alternatively, the pocket can be integrally formed in the excreta management device, for example being provided by a slit in the material of the bag. The slit is provided in a suitable desired position onto the opposing surface of the bag, and typically runs parallel to the transverse axis, thereby defining an opening for finger insertion. Of course, the liquid impermeability of the bag should be guaranteed, hence the slit could typically interest only an outer layer in a multilayer material structure constituting the bag, or at least constituting part of the bag structure where the slit and the opening for finger insertion have to be provided.

Of course, the alternative means for holding the excreta management device disclosed so far, in addition or as an alternative to their use as means for handling the device for application to and/or removal from the wearer's body, can also be provided to expand the bag into the desired three-dimensional shape after application of the device to the wearer's body, by simply inserting a finger in the finger insertion opening and pulling.

The opening 140 is formed on the wearer-facing surface 110 of the device 100 as shown in FIGS. 1 to 3 in order to receive excreta such as urine and/or fecal materials from an excretory orifice of the wearer prior to storage within the bag 130. The opening 140 is surrounded by the adhesive flange 150 and may be provided in any shape or size, such as circular, oblong, heart shaped and may be symmetrical or asymmetrical, preferably the opening has an oblong configuration either in the longitudinal direction or in the transversal direction.

The adhesive flange 150 is provided at the periphery of the opening 140 for adhesive attachment of the excreta management device 100 to the skin around the excretory orifice of a wearer. The adhesive flange 150 is attached to the wearer-facing surface 110 of the excreta management device 100 by means known to the person skilled in the art, such as adhesives, heat bond, or the like. The adhesive flange 150 may be provided in any shape and preferably has a symmetrical slightly oblong shape in the longitudinal direction or in the transversal direction shown in FIG. 1. Such suitable shapes include, but are not limited to: triangle shape; circle or oval shape; semicircle shape; sector shape; square, rectangular or diamond shape; pentagon shape or any combination of the above. The adhesive flange 150 typically comprises an adhesive layer and a substrate to support the adhesive layer.

FIGS. 7(a) and 7(b) show a preferred embodiment of an adhesive flange which is used for the excreta management device 100. The adhesive flange 300 shown in FIG. 7 has a longitudinal centerline L3 and a transverse centerline T3 which is perpendicular to the longitudinal centerline L3. The term "longitudinal", when used for the adhesive flange 300, refers to a line, axis or direction in the plane of the adhesive flange 300 that is substantially parallel to the longitudinal direction L1 of the excreta management device 100 when the adhesive flange 300 is attached to the excreta management device 100. The terms "transverse" or "lateral", when used for the adhesive flange 300, refer to a line, axis or direction which lies within the plane of the adhesive flange 300 that is generally perpendicular to the longitudinal direction. The adhesive flange 300 has two surfaces; one is a wearer-facing surface 310 and the other is an opposing surface 320. The wearer-facing surface 310 is the surface of the adhesive flange 300 which is generally oriented toward the wearer when the adhesive flange 300 is attached to the skin of a wearer. The wearer-facing surface 310 typically at least partially comes in contact with the wearer's skin during attachment of the adhesive flange 300 to the wearer's skin.

The opposing surface 320 is the surface of the adhesive flange 300 which is generally oriented away from the wearer when the adhesive flange 300 is attached to the skin of a wearer. The adhesive flange 300, preferably, is attached to the wearer-facing surface 110 of the excreta management devise 100 such that the longitudinal centerline L3 of the adhesive flange 300 corresponds to the longitudinal centerline L1 of the device 100. The adhesive flange 300 has an outer periphery 330 and an inner periphery 340, and comprises an adhesive layer 350 and a substrate 360 to support the adhesive layer 350. The inner periphery 340 of the adhesive flange 300 defines a generally circular aperture that is substantially aligned with the opening 140 of the bag 130 when the adhesive flange 300 is attached to the bag 130.

The adhesive flange 300 may be provided in any size depending on the wearer group for which the excreta management device 100 is intended. The overall length L of the adhesive flange 300 is measured along the longitudinal centerline L3 as shown in FIG. 7(a). The adhesive flange 300 may have an overall length L of between about 70 mm and about 120 mm if the adhesive flange 300 is used for the excreta management device designed for adult wearers. In addition, the adhesive flange 300 may have an overall length L of between about 40 mm and about 80 mm if the adhesive flange 300 is used for the excreta management device designed for infant wearers. The overall width W of the adhesive flange 300 is measured along the transverse centerline T3 as shown in FIG. 7(a). The adhesive flange 300 may have an overall width W of between about 100 mm and about 200 mm if the adhesive flange 300 is used for the excreta management device designed for adult wearers. In addition, the adhesive flange 300 may have an overall width W of between about 60 mm and about 130 mm if the adhesive flange 300 is used for the excreta management device designed for infant wearers. The flange width FW of the adhesive flange 300 is measured from the outer periphery 330 to the inner periphery 340 along the longitudinal centerline L3 as shown in FIG. 7(a). The adhesive flange 300 may have a flange width FW of between about 10 mm and about 30 mm if the adhesive flange 300 is used for the excreta management device designed for adult wearers. In addition, the adhesive flange 300 may have a flange width FW of between about 6 mm and about 20 mm if the adhesive flange 300 is used for the excreta management device designed for infant wearers.

Construction of the adhesive flange 300 according to the particular size parameters given above results in a product with increased comfort and effectiveness. For example, if the adhesive flange 300 is too smaller than the particular size given above, it is difficult to sufficiently keep the excreta management device 100 attached to the desired area of the skin of a wearer while the device 100 is worn. This is because the area of the adhesive layer 350 is not so large as to maintain the attachment of the device 100 to the wearer's skin during use of the device 100. Such an insufficient attachment of the device 100 may cause leakage of excreta when excretion occurs. In contrast, if the adhesive flange 300 is too bigger than the particular size given above, it is difficult to make the packaging of the excreta management device 100 compact. Such an unnecessary big size of the package of the device 100 may cause the costs for transport and packaging product to increase. In addition, if the adhesive flange 300 is too big, the contact area of the adhesive layer 350 constituting the adhesive flange 300 with the wearer's skin also tends to become too big. Such an unnecessary big contact area of the adhesive layer 350 with the wearer's skin may result in providing the wearer with pain when the device 100 is removed from the wearer's skin.

The substrate 360 of the adhesive flange 300 should be made of soft, flexible and malleable material to allow easy placement of the adhesive flange 300 to the skin of a wearer. In addition, the substrate 360 of the adhesive flange 300 may be made of a hydrophobic material and/or a breathable material. Suitable materials for the substrate 360 of the adhesive flange 300 include but are not limited to nonwoven materials, and foams, such as open celled thermoplastic foams. An open-cell foam having a thickness within the general range of about 0.5 to 10 millimeters (preferably about 2 millimeters) has been found particularly effective. Other foam materials or other suitable plastics sheet materials having the described properties of such foams (i.e., softness, pliability, stretchability, contractability, breathability, and hydrophobicity) might be used.

Figure 14:
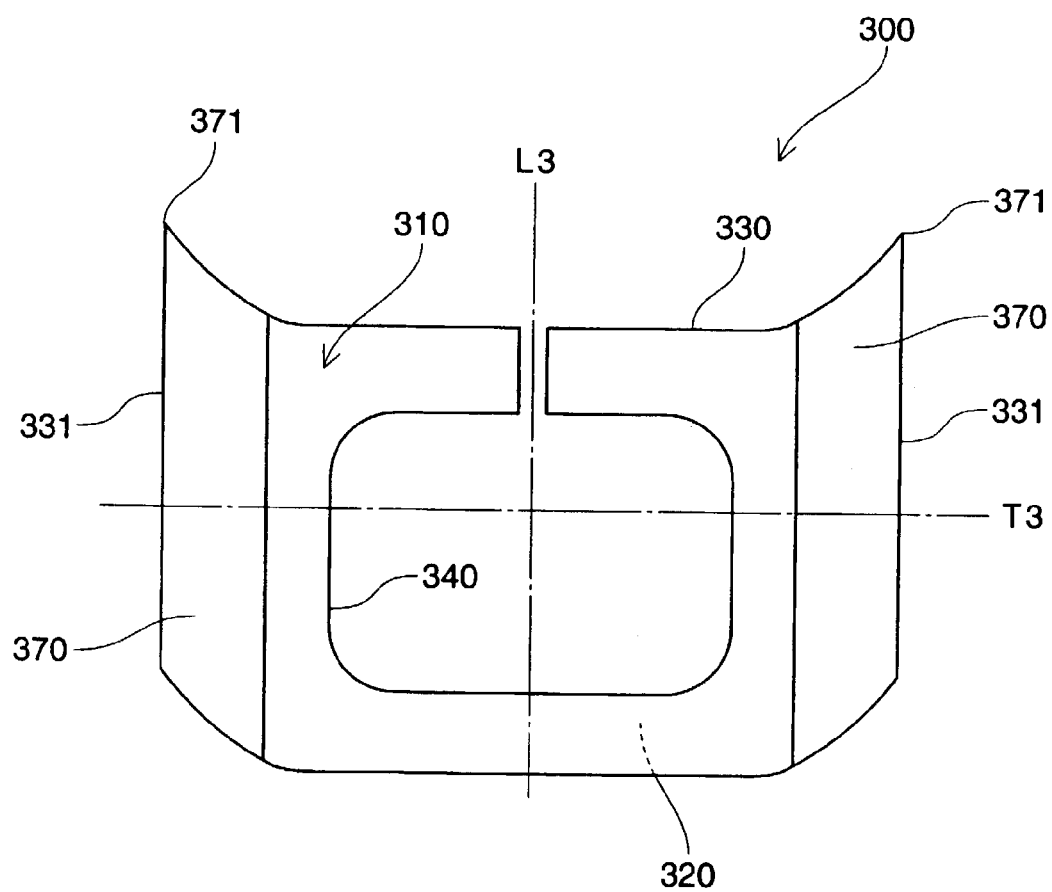
FIG. 14 is a top plan view of another embodiment of an adhesive flange.

The adhesive layer 350 of the adhesive flange 300 comprises a body-compatible adhesive. The adhesive layer 350 is used in order to fix the adhesive flange 300 with the skin of a wearer. Preferably, the adhesive layer 350 is covered with a release means to protect the adhesive layer 350 from contamination before use, such as siliconized paper or film. The adhesive layer 350 may cover the entire substrate 360, or alternatively, may partially cover the substrate 360 such that adhesive flange 300 has at least one, preferably a plurality of non-adhesive portions as removal tabs 370 to remove the excreta management device 100 from the skin of a wearer easily. The removal tabs 370 may be adhesive free or may contain inactivated or covered adhesives. The removal tabs 370 help users remove the device 100 from the skin of a wearer. In addition, the removal tabs 370 help users grip the device 100 for the attachment of the device 100 to the wearer's skin. In another embodiment shown in FIG. 14, the adhesive flange 300 has a generally rectangular shape, and the removal tabs 370 are provided along both side edges 331 extending in the longitudinal direction such that each of the removal tabs 370 has a sharp corner 371. The sharp corner 371 of the removal tab 370 helps users easily grasp the removal tab 370 in order to peel the adhesive flange 300 off the skin of a wearer.

Any medically approved water resistant pressure sensitive adhesive may be used for the adhesive layer 350 constituting the adhesive flange 300 to attach the device 100 to the skin of a wearer, such as hydrocolloid adhesives and hydrogel adhesives. Particularly effective adhesives in providing the desired adhesive properties to secure the adhesive flange 300 to the skin of a wearer around the sensitive excretory orifice area, while allowing for relatively painless application and removal, are hydrophillic hydrogels formed from crosslinking polymers with a plasticizer to form a three-dimensional matrix.

The adhesive can be applied to the substrate 360 of the adhesive flange 300 by any means known in the art such as slot coating, spiral, or bead application or printing in order to form the adhesive layer 350. Typically the adhesive is applied at a basis weight of from 20 g/m2 to 2500 g/m2, preferably from 500 g/m2 to 2000 g/m2, more preferably from 700 g/m2 to 1500 g/m2 depending on the end use envisioned. For example, for excreta management devices to be used for children, the amount of adhesive may be less than for excreta management devices designed for active adult incontinence sufferers.

The adhesive flange 300 shown in FIGS. 7(a) and 7(b) comprises a continuous adhesive layer 350 and a substrate 360 having a base-slit 361. The base-slit 361 extends from the outer periphery 330 to the inner periphery 340 along the longitudinal centerline L3 that corresponds to the longitudinal centerline L1 of the excreta management device 100 when the adhesive flange 300 is attached to the bag 130. Alternatively, the adhesive flange 300 may comprise an adhesive layer 350 having a surface-slit 351 and a continuous substrate 360 as shown in FIGS. 8(a) and 8(b). The surface-slit 351 extends from the outer periphery 330 to the inner periphery 340 along the longitudinal centerline L3. The term "slit", as used herein, refers to a narrow or wide empty space between two objects or two parts of an object. Such a slit includes a gap, a crack, a notch, a channel, a trench, and the like. The term "base-slit", as used herein, refers to a slit provided to a substrate constituting an adhesive flange. The term "surface-slit", as used herein, refers to a slit provided to an adhesive layer constituting an adhesive flange.

While an excreta management device comprising an adhesive flange is worn, wearer's motion, such as walking, crawling, running and sitting, causes intense muscle and/or skin movements in the area to which the adhesive flange 300 is attached, e.g., a perianal area. Similarly, a defecation motion leads to intense muscle and/or skin movements in the vicinity of an excretory orifice. Materials conventionally utilized for the substrate constituting the adhesive flange, such as nonwoven materials, foams, plastic films or the like, typically does not have such elasticity that the adhesive flange conforms to various skin movement. For example, the excreta management device is attached and positioned between the wearer's legs. In such a case, wearer's motion such as walking, crawling, running or the like, often causes stress on the adhesive flange of the device to twist the adhesive flange at the area between the wearer's legs and to detach the adhesive flange from the wearer's skin. Such stress on the adhesive flange is typically developed by asymmetric movement of left and right halves of wearer's skin at the crotch region. The base-slit 361 extending along the longitudinal centerline L3 prevents the stress from being developed on the adhesive flange 300 not to cause undesirable detachment of the adhesive flange 300 from the wearer's skin. Thus, the excreta management device 100 comprising the adhesive flange 300 having the base-slit 361 does not cause incomplete-collection/leakage of excreta resulting from the undesirable detachment of the adhesive flange 300 from the wearer's skin, and does not provide the wearer with skin pain that tends to occur when the adhesive flange 300 is detached. The base-slit 361 also functions as a vent hole which facilitates expansion of the bag 130 by introducing air into the bag 130 therethrough. In addition, forming the base-slit 361 to the substrate 360 reduces cost of raw material for the substrate 360. Preferably, the base-slit 361 is positioned at a perineum (i.e., region between an anus and a urethral orifice) when the device 100 is worn. The substrate 360 may have two base-slits 361 oppositely disposed with respect to the opening 140 along the longitudinal centerline L3 when the adhesive flange 300 is attached to the device 100 as shown in FIG. 7(a), or may have either of the slits.

The adhesive flange 300 may have the surface-slit 351 extending from the outer periphery 330 to the inner periphery 340 along the longitudinal centerline L3 instead of the base-slit 361 as shown in FIGS. 8(a) and 8(b). The surface-slit 351 is positioned on the adhesive flange 330 to be positioned at a perineum (i.e., region between an anus and a urethral orifice) when the device 100 is worn such that the adhesive layer 350 does not contact with a perineum. Such arrangement of the surface-slit 351 does not provide the wearer with discomfort resulting from contact of the adhesive layer 350 with a perineum which is typically very sensitive. Particularly, in case of female wearers having genitalia at a perineum, contact of a foreign object such as an adhesive flange to a perineum provides serious discomfort. Therefore, the adhesive flange 300 having the surface-slit 351 is extremely desirable/comfortable for female wearers. In addition, even if discharged urine flows to a perineum, the adhesive layer 350 does not deteriorate since existence of the surface-slit 351 substantially avoids contact of the adhesive layer 350 with urine at a perineum during use of the device 100. Thus, the adhesive flange 300 having the surface-slit 351 prevents undesirable detachment of the adhesive flange 300 resulting from deterioration of the adhesive layer 350 at a perineum. In addition, forming the surface-slit 351 to the adhesive layer 350 reduces cost of raw material for the adhesive layer 350. The surface-slit 351 also functions as a vent hole which facilitates expansion of the bag 130 by introducing air into the bag 130 therethrough. In another embodiment, the surface-slit 351 may be filled with filler 390 as shown in FIG. 8(c). The filler 390 may be made of soft, flexible, compliant and malleable material so as not to provide the wearer with skin irritation. Suitable materials for the filler 390 include but are not limited to absorbent or non-absorbent foams, sponges, cotton, tissue, comminuted wood pulp (e.g., airfelt), or any other known compliant material to human skin, or mixtures thereof.

Figure 5:
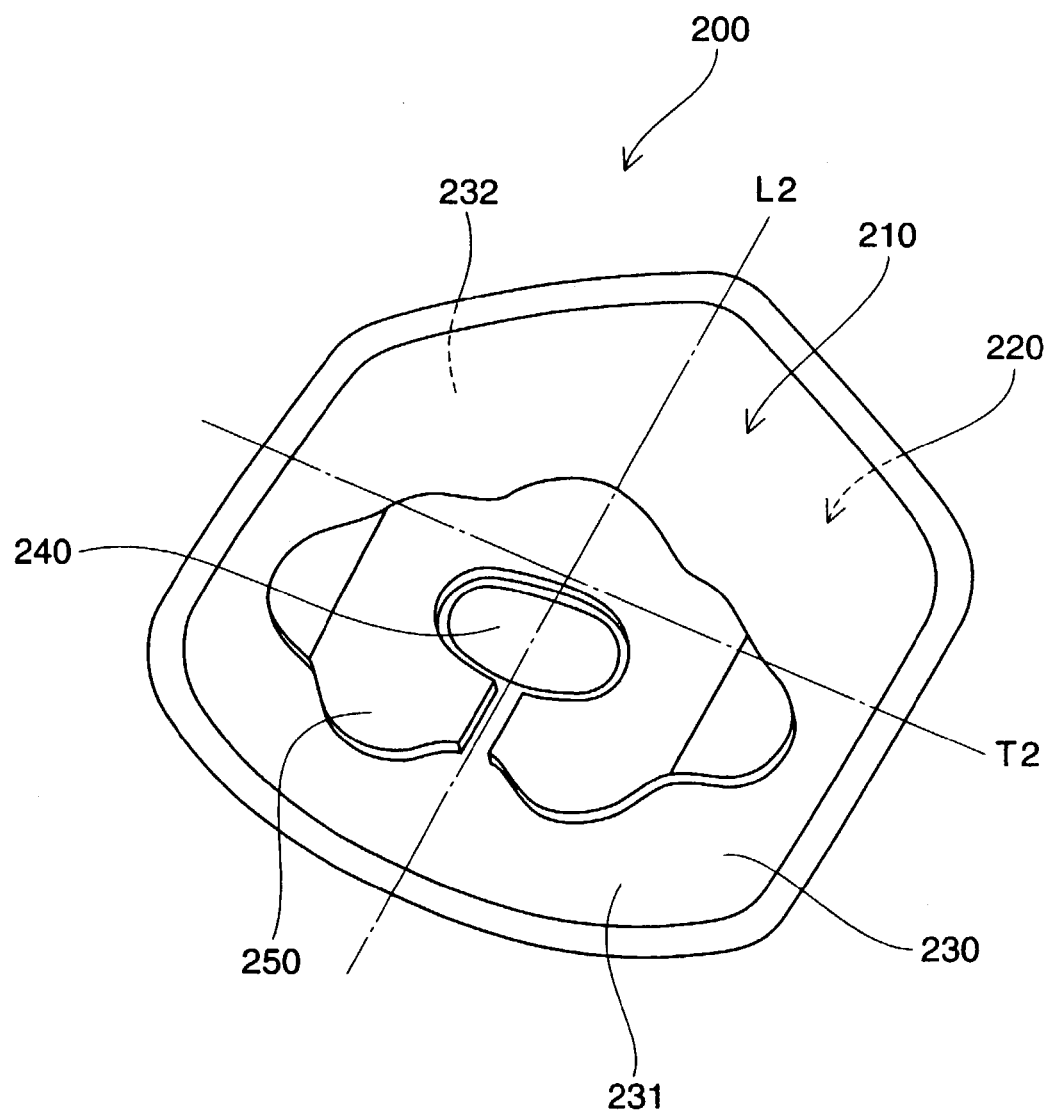
FIG. 5 is a perspective view showing the wearer-facing surface of another embodiment of an excreta management device of the present invention.
Figure 10:
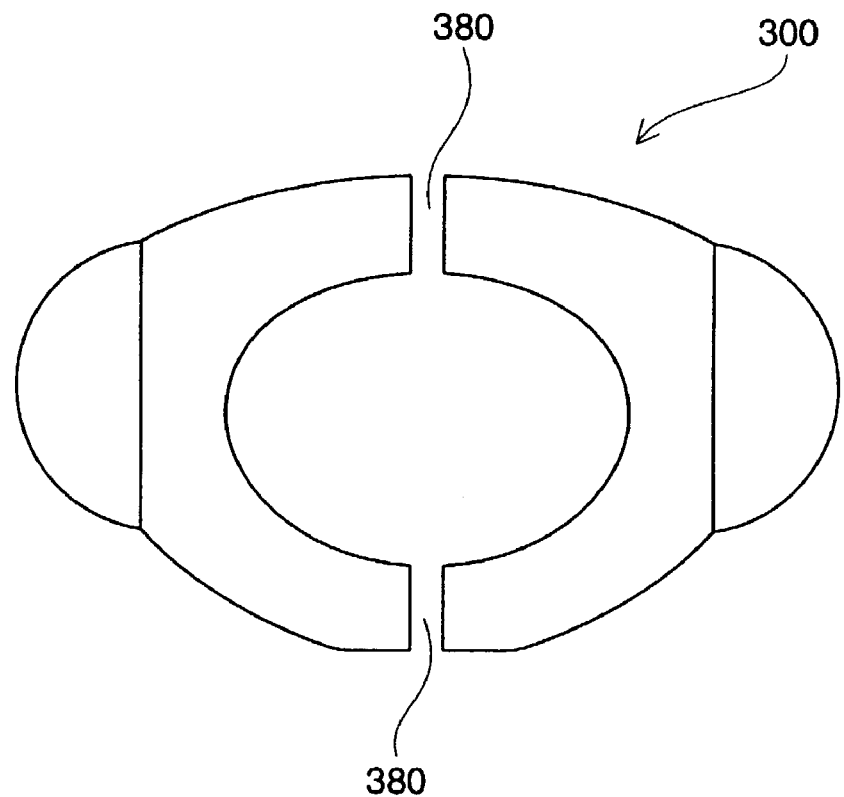
FIG. 10 is a top plan view of another embodiment of an adhesive flange.
Figure 11:
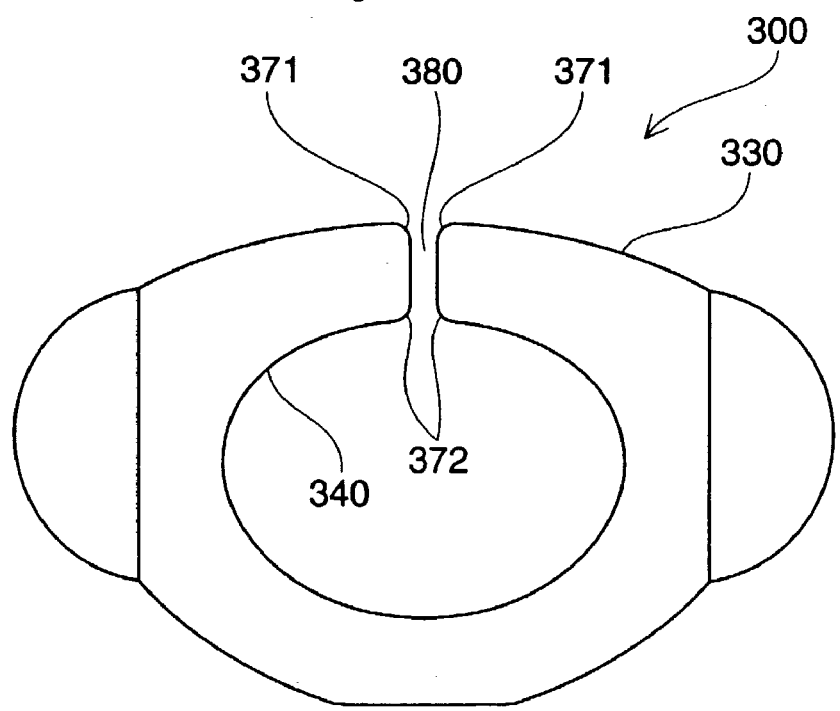
FIG. 11 is a top plan view of another embodiment of an adhesive flange.
Figure 12:
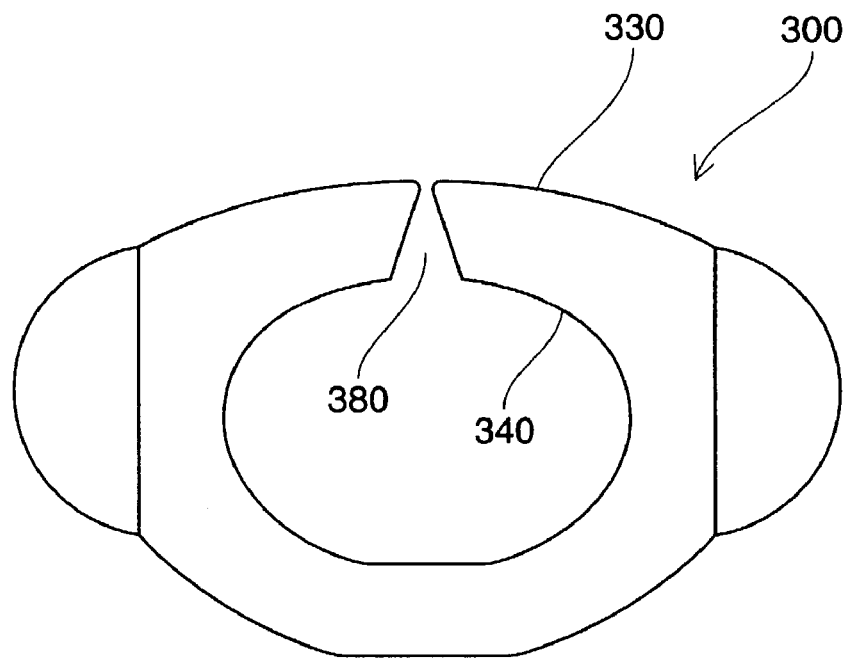
FIG. 12(a) is a top plan view of another embodiment of an adhesive flange.
FIG. 12(b) is a top plan view of another embodiment of an adhesive flange.
Figure 12:
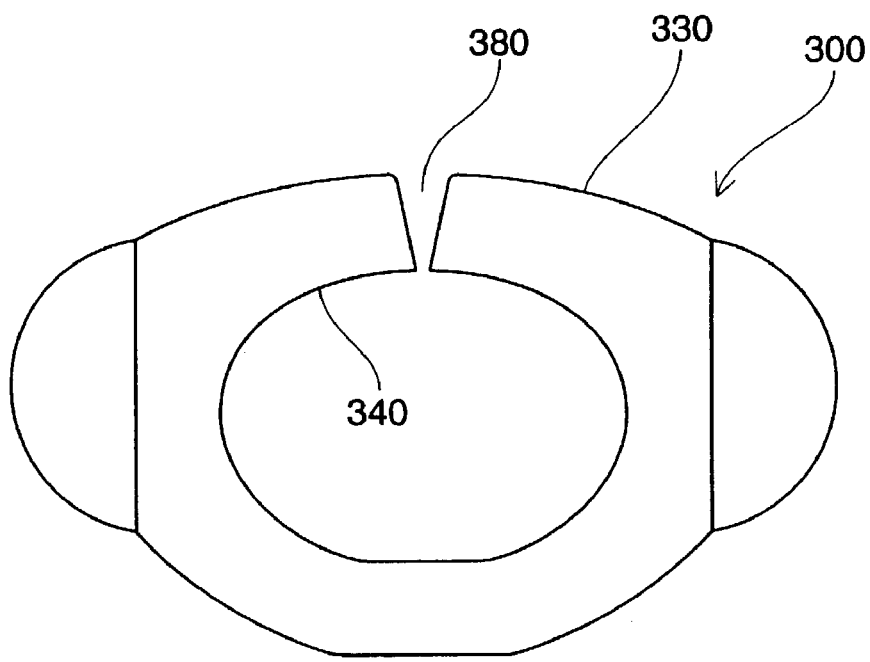
Figure 13:
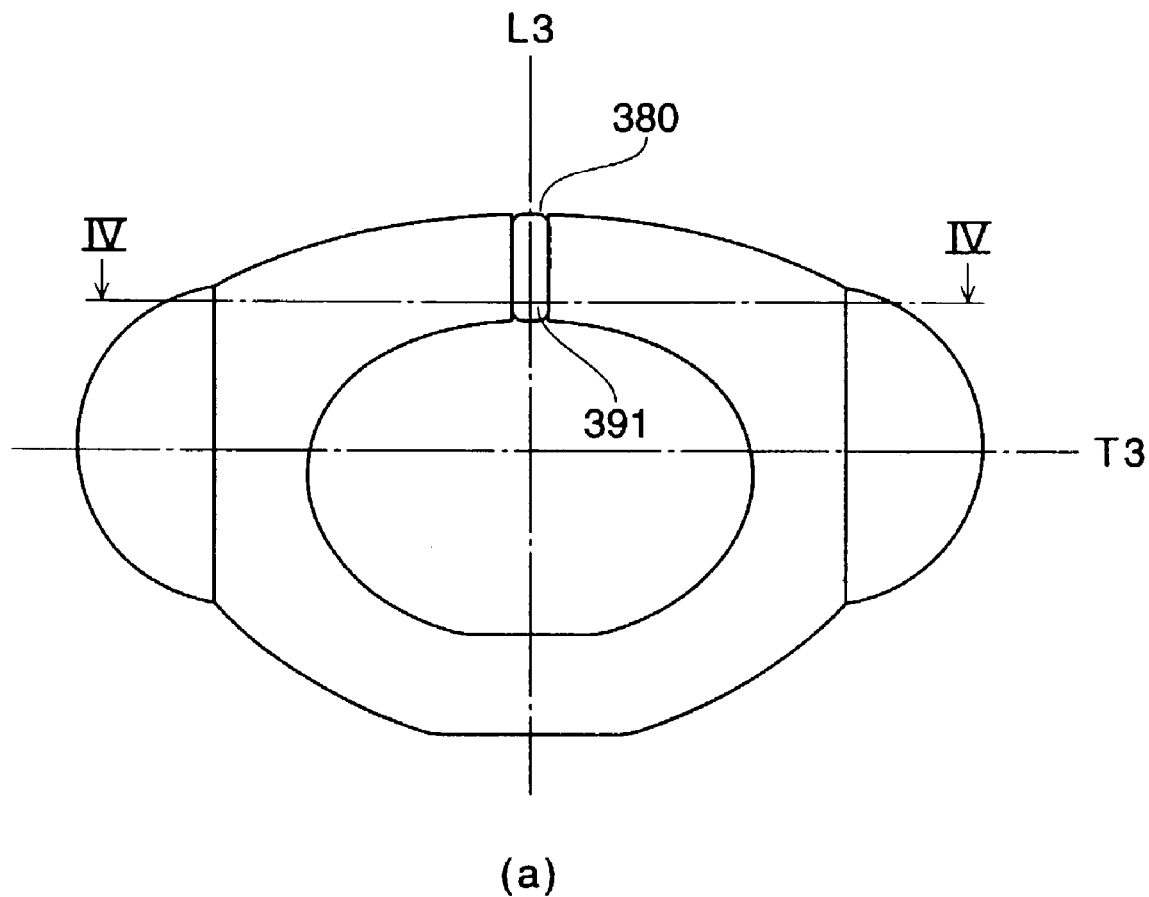
FIG. 13(a) is a top plan view of another embodiment of an adhesive flange.
FIG. 13(b) is a cross-sectional view taken along line IV—IV of FIG. 13(a)
Figure 13:
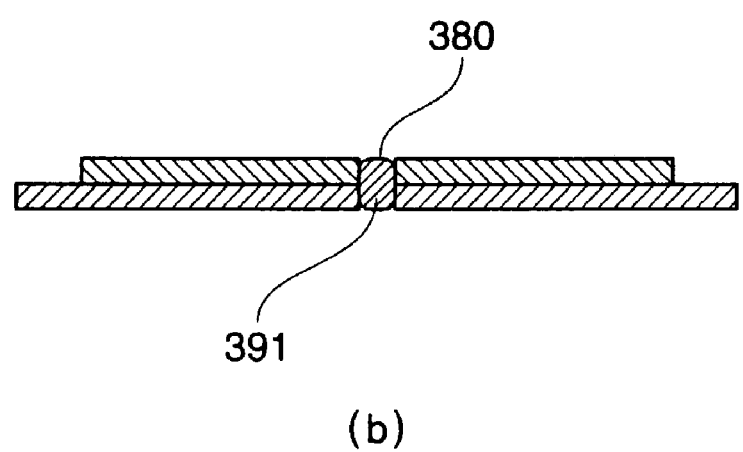

The adhesive flange 300, preferably, comprises an adhesive layer 350 having a surface-slit 351 and a substrate 360 having a base-slit 361 as shown in FIGS. 9(a) and 9(b) (FIGS. 1, 2 and 5 also show the adhesive flange comprising an adhesive layer having a surface-slit and a substrate having a base-slit.). Both the surface-slit 351 and the base-slit 361 extend from the outer periphery 330 to the inner periphery 340 along the longitudinal centerline L3 that corresponds to the longitudinal centerline L1 of the excreta management device 100 when the adhesive flange 300 is attached to the device 100. Preferably, the surface-slit 351 is continuously connected with the base-slit 361 to form a flange-slit 380. The term "flange-slit", as used herein, refers to a slit formed by continuously connecting a surface-slit with a base-slit. More preferably, the flange-slit 380 is positioned between an anus and a urethral orifice (i.e., a perineum) when the device 100 is worn. Forming the flange-slit 380 to the adhesive flange 300 provides the excreta management device 100 with the above-mentioned benefits resulting from forming each of the surface-slit 351 and the base-slit 361, and further, it reduces cost of raw materials for both the adhesive layer 350 and the substrate 360. The flange-slit 380 also functions as a vent hole which facilitates expansion of the bag 130 by introducing air into the bag 130 therethrough. The adhesive flange may have two flange-slits 380 oppositely disposed with respect to the opening 140 along the longitudinal centerline L3 when the adhesive flange 300 is attached to the device 100 as shown in FIG. 10, or may have either of the slits. In another embodiment, the flange-slit 380 may be formed such that the corners 371 at the outer periphery 330 and/or the corners 372 at the inner periphery 340 are rounded as shown in FIG. 11. The rounded corners 371 and/or 372 prevent the adhesive flange 300 from readily coming off the wearer's skin during use of the device 100 because the stress applied to the rounded corners 371 and/or 372 is distributed not to cause peeling of the adhesive flange 300. In yet another embodiment, the flange-slit 380 may be formed such that the width of the flange-slit 380 increases from the outer periphery 330 toward the inner periphery 340 as shown in FIG. 12(a). Alternatively, the flange-slit 380 may be formed such that the width of the flange-slit 380 may decreases from the outer periphery 330 toward the inner periphery 340 as shown in FIG. 12(b). In still yet another embodiment, the flange-slit 380 may be filled with filler 391 as shown in FIGS. 13(a) and 13(b). The filler 391 should be made of soft, flexible, compliant and malleable material so as not to provide the wearer with skin irritation. Suitable materials for the filler 391 include but are not limited to absorbent or non-absorbent foams, sponges, cotton, tissue, comminuted wood pulp (e.g., airfelt), or any other known compliant materials to human skin, or mixtures thereof.

The surface-slit 351, the base-slit 361 and the flange-slit 380 may be provided in any size depending on the wearer group for which the excreta management device 100 is intended. The width of the slits 351, 361 and 380 is measured along the transverse centerline T3. The slits 351, 361 and 380 may have an overall width of between about 1 mm and about 20 mm if the adhesive flange 300 is used for the excreta management 100 device designed for adult wearers. In addition, the slits 351, 361 and 380 may have an overall width of between about 1 mm and about 10 mm if the adhesive flange 300 is used for the excreta management device 100 designed for infant wearers. The length of the slits 351, 361 and 380 is measured along the longitudinal centerline L3. Such a length of the slits 351, 361 and 380 substantially corresponds to the flange width FW shown in FIG. 7(a).

Figure 15A:
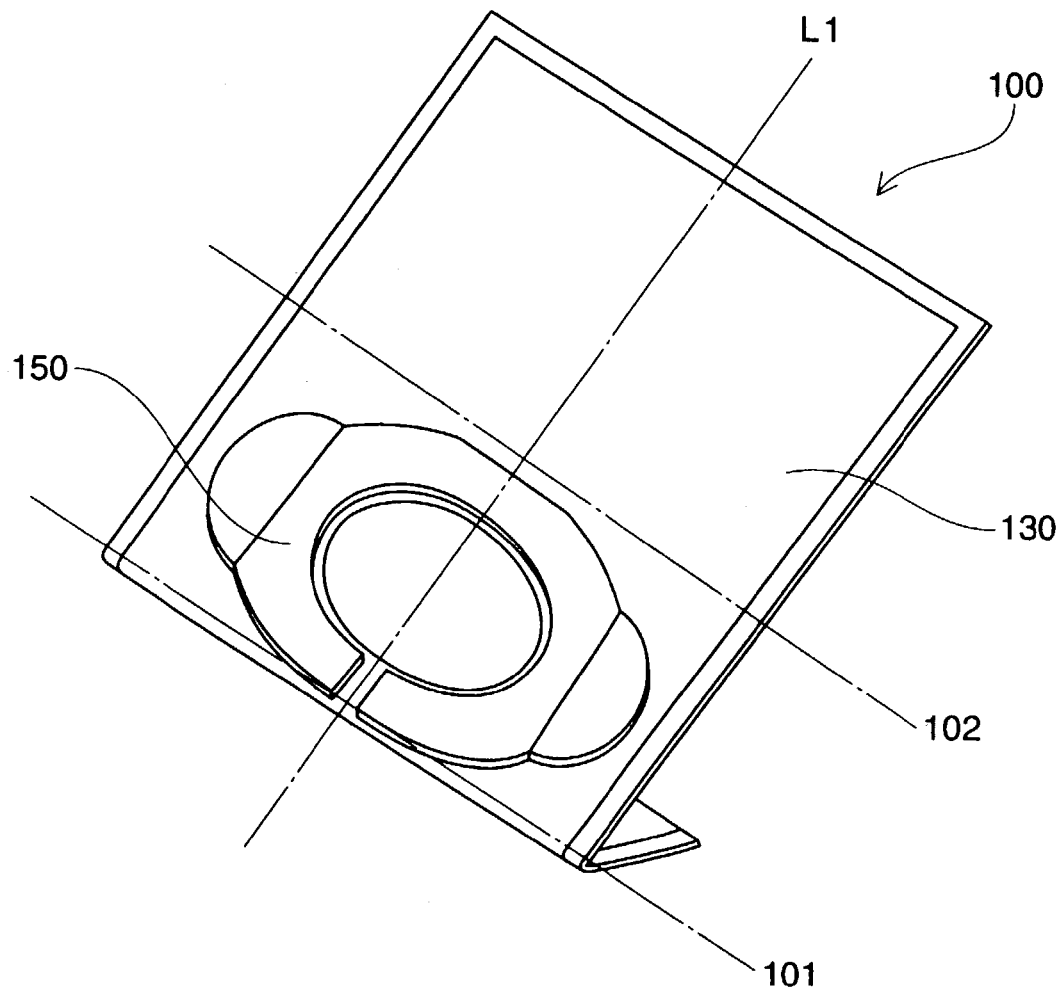
FIG. 15(a) is a first schematic perspective view of the excreta management device of FIG. 1 when the device is folded for packaging.
Figure 15B:
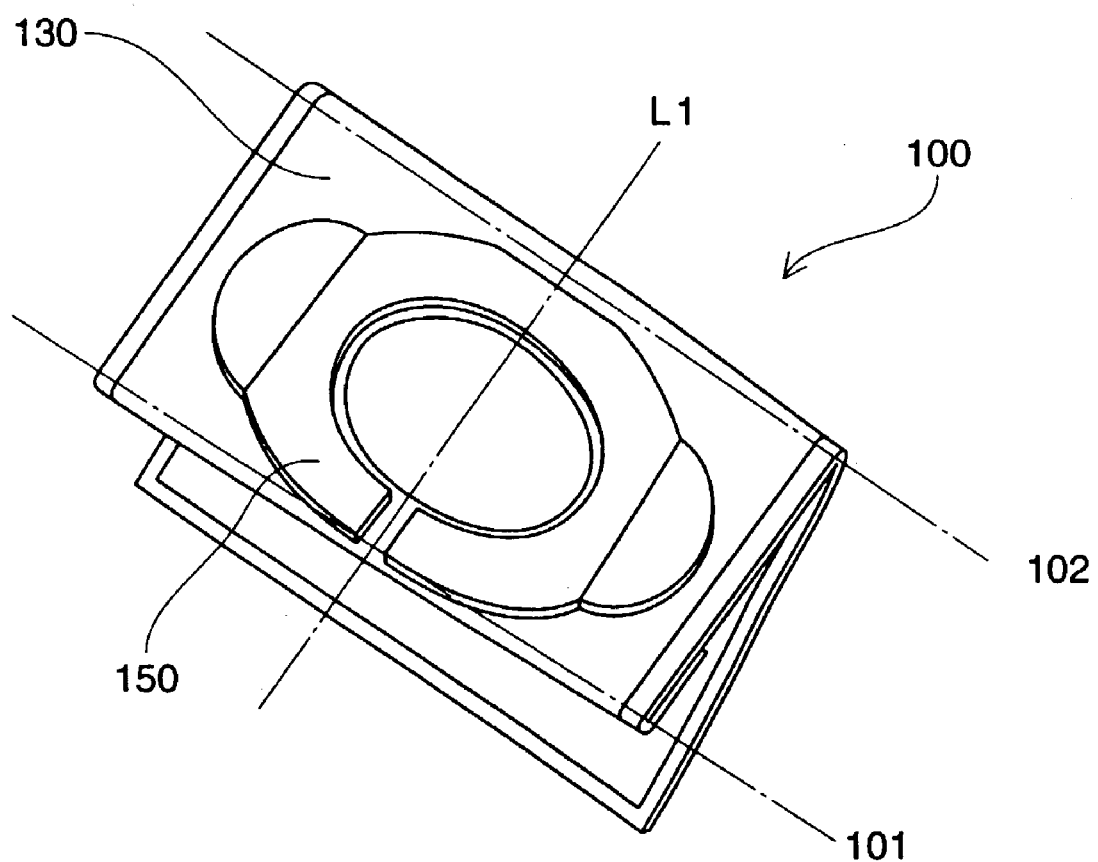
FIG. 15(b) is a second schematic perspective view of the excreta management device of FIG. 1 when the device is folded for packaging.
Figure 15C:
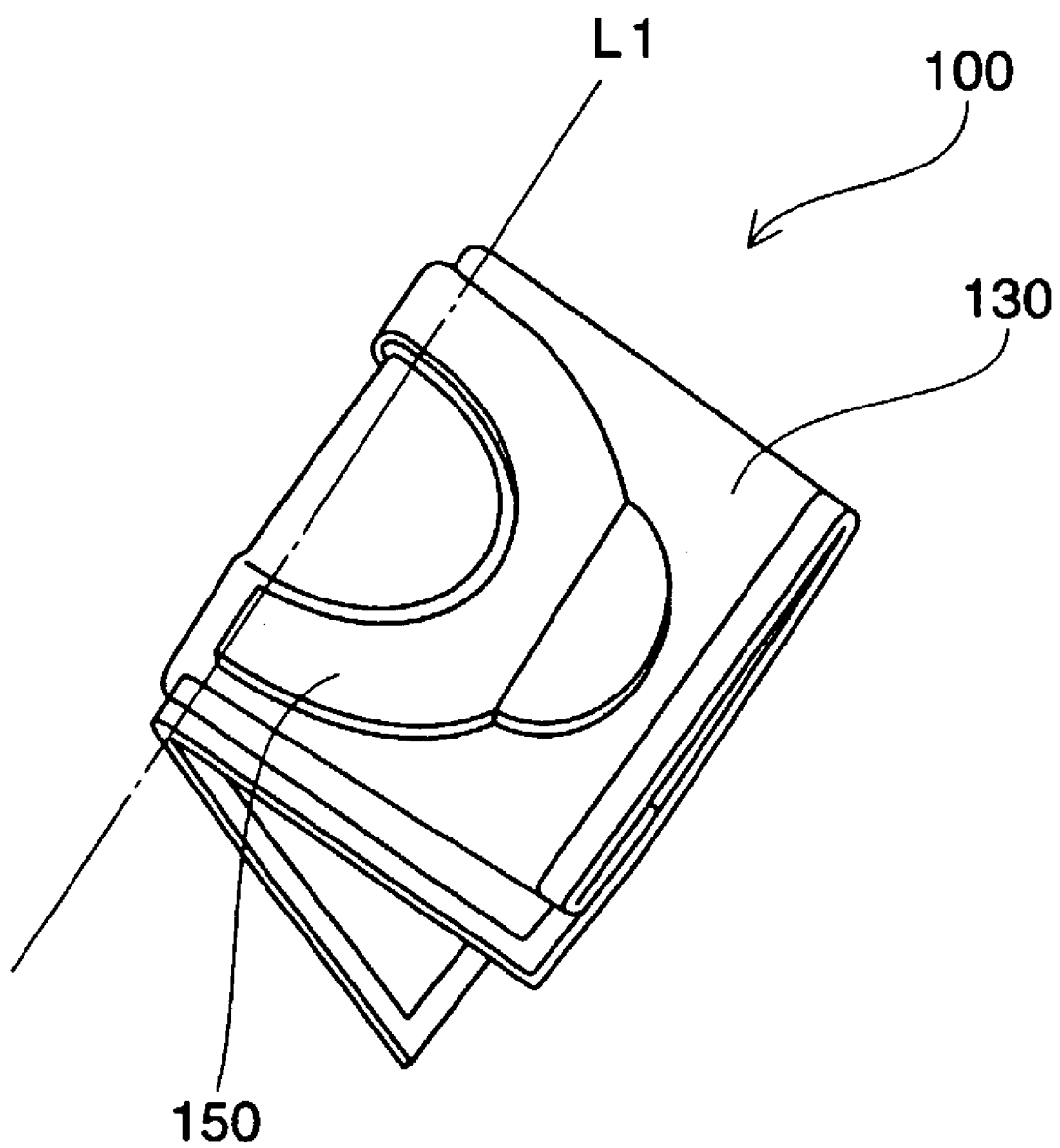
FIG. 15(c) is a third schematic perspective view of the excreta management device of FIG. 1 when the device is folded for packaging.

In a preferred embodiment, the excreta management device 100 is provided in a particular form prior to use of the device 100. In that form, the flexible bag 130 constituting the device 100 is transversely folded along the folding line 101 first as shown in FIG. 15(a). The bag 130, then, is further transversely folded along the folding line 102 as shown in FIG. 15(b). Finally, the bag 130 and the adhesive flange 150 are longitudinally folded along the longitudinally centerline L1 as shown in FIG. 15(c) for the easy placement of the device 100, e.g., between the buttocks of the wearer. The folded device 100 is held by the user as shown in FIG. 16 for the attachment of the device 100 to the skin of a wearer. The bag 130 may be folded such that the bag 130 is substantially disposed between the two pieces of the folded adhesive flange 150. The folded form of the device 100 shown in FIG. 16 provides numerous advantages. While each of the components of the device 100 (i.e., the bag 130 and the adhesive flange 150) is flexible so as to conform movement of the wearer's skin and to provide the wearer with comfort, such flexibility of the device 100 makes the attachment of the device 100 to the wearer's skin difficult because the user cannot sufficiently press the adhesive flange 150 constituting the device 100 to the wearer's skin during the attachment of the device 100. Folding the device 100 as shown in FIGS. 15(a) to 15(c) provides the device 100 with such rigidity that the user can sufficiently press the adhesive flange 150 constituting the device 100 to the desired area around the excretory orifice of the wearer such as the perianal area (or urogenital area). Thus, the folded device 100 contributes to the complete attachment of the device 100 to the wearer's skin. Folding the device 100, further, facilitates a compact packaging form of the device 100. This results in reducing the costs for transport and packaging material. In addition, the unfolded device 100 may cover the skin of a wearer such that the user placing the device 100 cannot sufficiently visually control placement of the device 100. The folded device 100 makes the attachment of the device 100 to the skin of a wearer easy.

Figure 17:
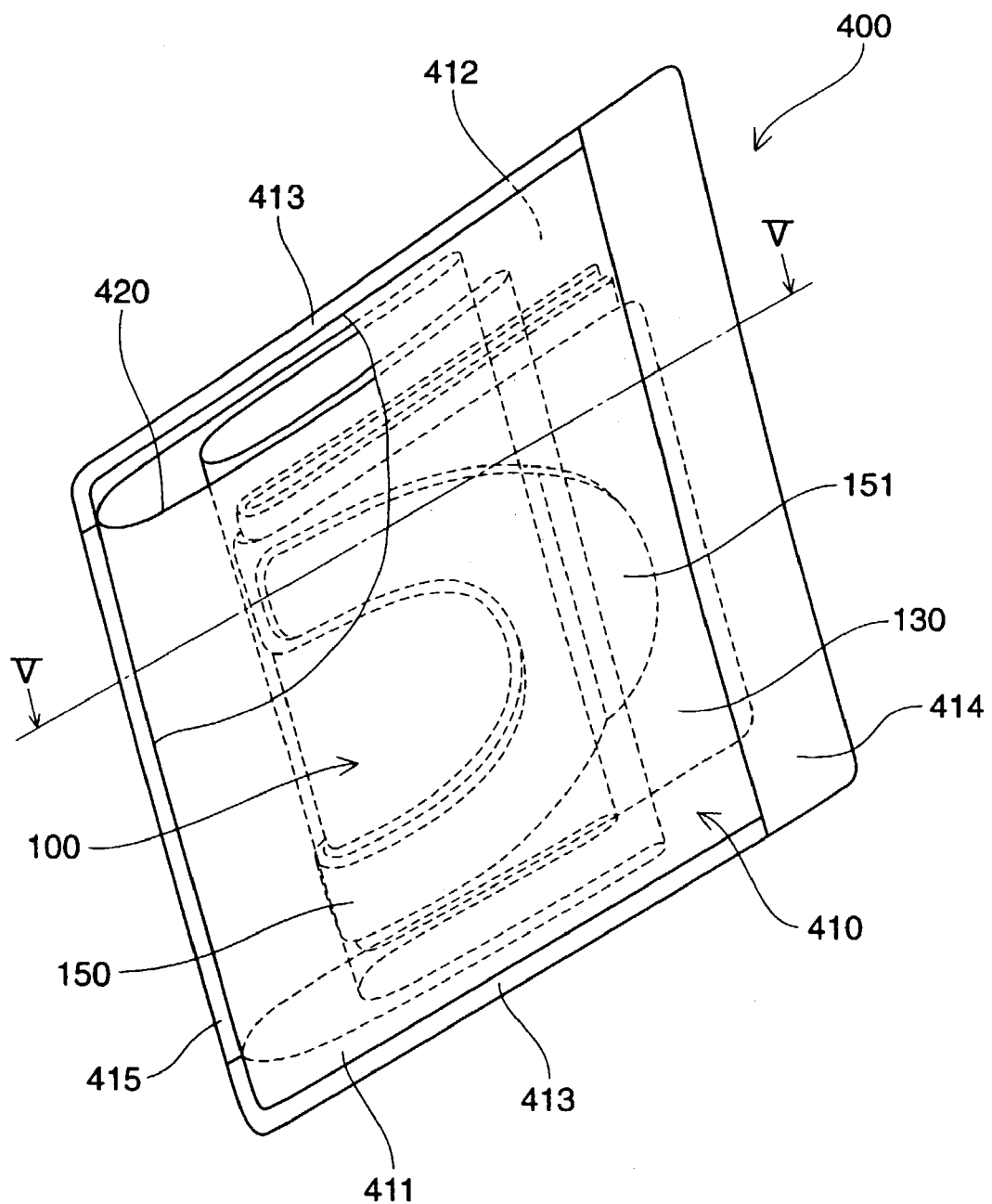
FIG. 17 is a perspective view of the package of the excreta management device of FIG. 1.
Figure 18:
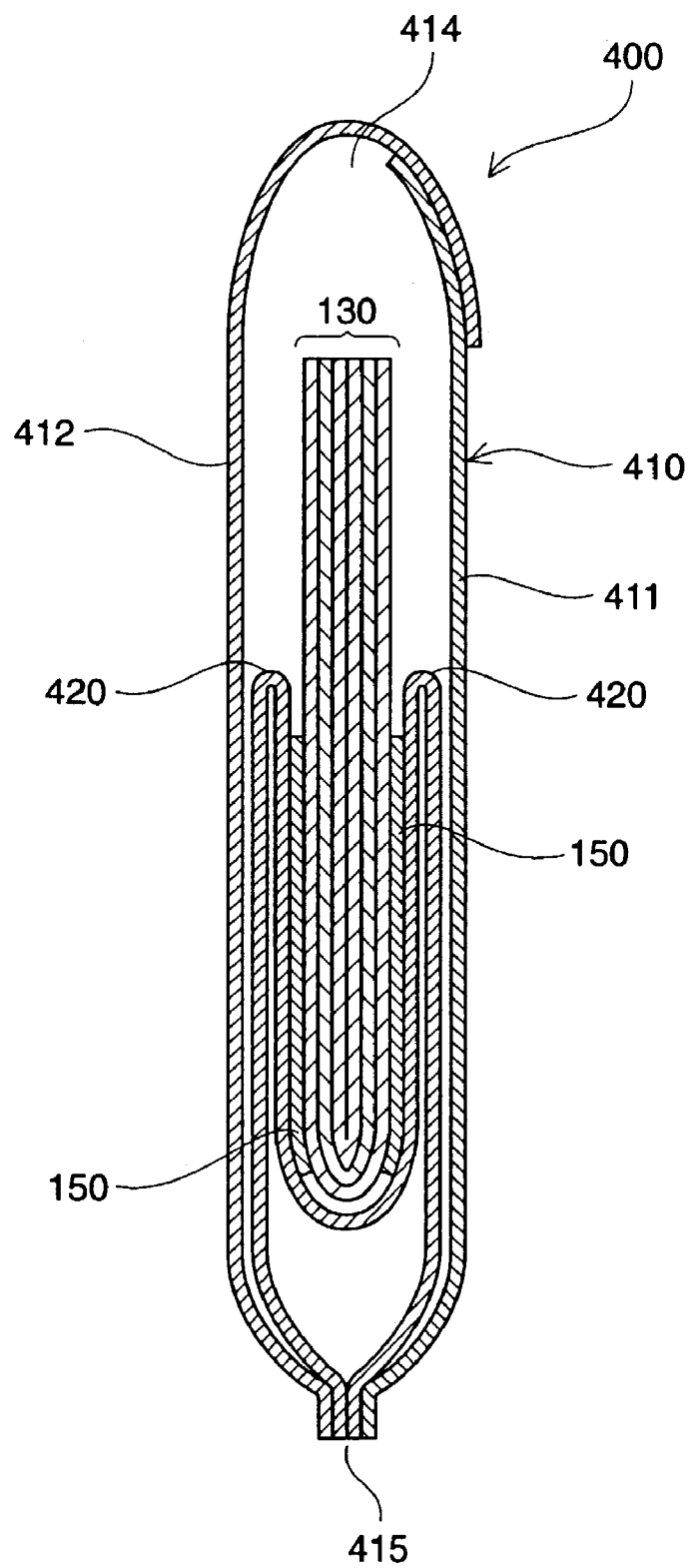
FIG. 18 is a cross-sectional view taken along line V—V of FIG. 17.
Figure 19:
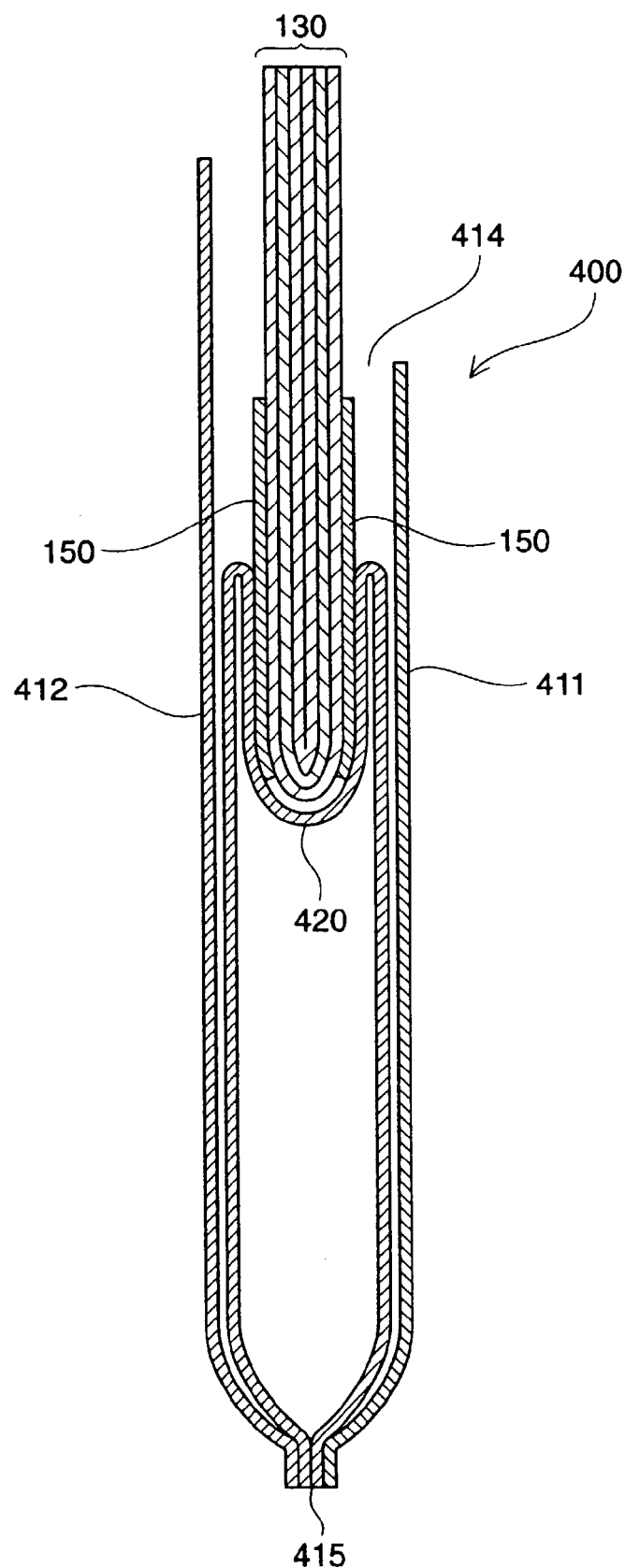
FIG. 19 is a cross-sectional view of the package of the excreta management device of FIG. 17 when the device is taken out from the package.

In a preferred embodiment, the excreta management device 100 may be packaged as shown in FIGS. 17 and 18. The package 400 shown in FIGS. 17 and 18 comprises an outer cover 410 and an inner release film 420 joined to the outer cover 410. The outer cover 410 comprises a first piece 411 and a second piece 412 sealed along side edges 413 and an end edge 415 by any means known to the person skilled in the art, such as heat seal in order to form a pouched shape. The package 400 further has an open edge 414. The first piece 411 and the second piece 412 are temporarily sealed at the open edge 414 by any means known to the person skilled in the art, such as adhesive such that a part of the first piece 411 and a part of the second piece 412 overlap with one another. The user can easily open the outer cover 410 in order to take out device 100 therefrom. The inner release film 420 is disposed at the inside of the outer cover 410 in order to completely cover the adhesive constituting the adhesive flange 150 of the device 100. Therefore, the adhesive constituting the adhesive flange 150 can be protected from contamination by the inner release film 420 before use of the device 100. The inner release film 420 is joined to the outer cover 410 at the end edge 415 opposite to the open edge 414 such that the inner release film 420 remains inside of the outer cover 410 when the device 100 is taken out from the package 400 by the user as shown in FIG. 19. The user opens the open edge 414 of the outer cover 410 first when the user uses the device 100. The user then grasps the tabs 151 of the device 100 and takes out the device 100 from the package 400. Because the inner release film 420 is joined to the outer cover 410 at the end edge 415, the adhesive flange 150 of the device 100 is separated from the inner release film 420 after the device 100 is taken out from the package 400, and the adhesive constituting the adhesive flange 150 is exposed for adhesive attachment of the device 100 to the skin of a wearer.

The use of an excreta management device 100 for placement of the device 100 according to the present invention preferably comprises the following steps:

(a) Opening the package 400 of the excreta management device 100;

(b) Taking out the device 100 from the package 400 while gripping the tabs 151 of the device 100 by using one hand as shown in FIG. 16;

(c) Supporting the body of a wearer, such as wearer's legs by using the other hand for placement of the device 100;

(d) Placing the device 100 in the area around the excretory orifice of the wearer such as the perianal area (or urogenital area) while holding the tabs 151 of the device 100;

(e) Letting the adhesive applied to the adhesive flange 150 of the device 100 attach to the area around the excretory orifice of the wearer while holding the tabs 151 of the device 100;

(f) Exerting force to press the device 100 toward the area around the excretory orifice of the wearer through the tabs 151 of the device 100;

(g) Pressing the entire adhesive provided on the adhesive flange 150 of the device 100 toward the area around the excretory orifice of the wearer;

(h) Unfolding the bag 130 of the device 100; and (i) Pulling the assistant tab 160 disposed on the bag 130 to expand the bag 130 into a three-dimensional shape.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable excreta management device having a longitudinal centerline, a transverse centerline, a wearer facing surface and an opposing surface, the disposable excreta management device comprising a flexible bag to contain excreta and an adhesive flange to attach the device to the body of a wearer, the flexible bag having an opening surrounded by the adhesive flange, the adhesive flange having an outer periphery and an inner periphery, the adhesive flange comprising an adhesive layer and a substrate, wherein the adhesive layer has a surface-slit extending from the outer periphery to the inner periphery along the longitudinal centerline, and the surface-slit is positioned between an anus and a urethra when the device is worn wherein the surface-slit is filled with filler.

2. A disposable excreta management device of claim 1 wherein the filler is foams, sponges, cotton, tissue, airfelt, or mixtures thereof.

3. The disposable excreta management device of claim 1 further comprising an assistant tab disposed on the opposing surface of the disposable excreta management device.

4. The disposable excreta management device of claim 1 wherein the flexible bag further comprises absorbent material disposed within the flexible bag.

5. The disposable excreta management device of claim 1 wherein the adhesive flange has a length of between about 40 mm to about 120 mm.

6. The disposable excreta management device of claim 1 wherein the adhesive flange has an overall width of between about 60 mm to about 200 mm.

7. The disposable excreta management device of claim 1 wherein the adhesive flange has a flange width of between about 6 mm to about 30 mm.

* * * * *

UNITED STATES PATENT AND TRADEMARK OFFICE
CERTIFICATE OF CORRECTION

| | | |
|---|---|---|
| PATENT NO. | : 7,101,357 B2 | Page 1 of 1 |
| APPLICATION NO. | : 10/367391 | |
| DATED | : September 5, 2006 | |
| INVENTOR(S) | : Masato Tanaka et al. | |

It is certified that error appears in the above-identified patent and that said Letters Patent is hereby corrected as shown below:

<u>Column 11</u>
Line 6, delete "devise" and insert -- device --.

Signed and Sealed this

Seventh Day of August, 2007

JON W. DUDAS
*Director of the United States Patent and Trademark Office*